(12) United States Patent
Shachal et al.

(10) Patent No.: US 8,334,510 B2
(45) Date of Patent: Dec. 18, 2012

(54) SCANNING ELECTRON MICROSCOPE, AN INTERFACE AND A METHOD FOR OBSERVING AN OBJECT WITHIN A NON-VACUUM ENVIRONMENT

(75) Inventors: Dov Shachal, Rehovot (IL); Rafi De Picciotto, Carmei Yosef (IL)

(73) Assignee: B-Nano Ltd., Omer (IL)

( * ) Notice: Subject to any disclaimer, the term of this patent is extended or adjusted under 35 U.S.C. 154(b) by 80 days.

(21) Appl. No.: 13/002,448

(22) PCT Filed: Jul. 2, 2009

(86) PCT No.: PCT/IL2009/000660
§ 371 (c)(1),
(2), (4) Date: Mar. 10, 2011

(87) PCT Pub. No.: WO2010/001399
PCT Pub. Date: Jan. 7, 2010

(65) Prior Publication Data
US 2011/0168889 A1    Jul. 14, 2011

Related U.S. Application Data

(60) Provisional application No. 61/077,955, filed on Jul. 3, 2008, provisional application No. 61/077,981, filed on Jul. 3, 2008, provisional application No. 61/077,977, filed on Jul. 3, 2008, provisional application No. 61/077,970, filed on Jul. 3, 2008.

(51) Int. Cl.
*H01J 37/28*    (2006.01)
*H01J 37/20*    (2006.01)
*G01N 23/00*    (2006.01)

(52) U.S. Cl. ........ 250/310; 250/306; 250/307; 250/311; 250/306 R; 250/492.2; 315/111.81

(58) Field of Classification Search .................. 250/310, 250/306, 307, 311, 396 R, 492.2; 315/111.81
See application file for complete search history.

(56) References Cited

U.S. PATENT DOCUMENTS
3,307,066 A    2/1967    Shapiro et al.
(Continued)

FOREIGN PATENT DOCUMENTS
EP    1 515 358 A2    3/2005
(Continued)

OTHER PUBLICATIONS

An International Search Report dated Nov. 18, 2009, which issued during the prosecution of Applicant's PCT/IL09/00660.

(Continued)

*Primary Examiner* — Nikita Wells
(74) *Attorney, Agent, or Firm* — Sughrue Mion, PLLC

(57) ABSTRACT

An interface, a scanning electron microscope and a method for observing an object that is positioned in a non-vacuum environment. The method includes: generating an electron beam in the vacuum environment; scanning a region of the object with the electron beam while the object is located below an object holder; wherein the scanning comprises allowing the electron beam to pass through an aperture of an aperture array, pass through an ultra thin membrane that seals the aperture, and pass through the object holder; wherein the ultra thin membrane withstands a pressure difference between the vacuum environment and the non-vacuum environment; and detecting particles generated in response to an interaction between the electron beam and the object.

61 Claims, 25 Drawing Sheets

U.S. PATENT DOCUMENTS

| | | | |
|---|---|---|---|
| 3,787,696 A | 1/1974 | Dao et al. | |
| 5,081,353 A | 1/1992 | Yamada et al. | |
| 5,811,803 A * | 9/1998 | Komatsu et al. | 250/310 |
| 5,898,269 A * | 4/1999 | Baum et al. | 313/542 |
| 6,005,540 A | 12/1999 | Shinjo et al. | |
| 6,410,923 B1 | 6/2002 | Crewe | |
| 6,610,980 B2 | 8/2003 | Veneklasen et al. | |
| 7,220,963 B2 | 5/2007 | Gross | |
| 8,164,057 B2 * | 4/2012 | Shachal | 250/307 |
| 2003/0178576 A1 | 9/2003 | Pan et al. | |
| 2004/0188611 A1 | 9/2004 | Takeuchi et al. | |
| 2006/0012785 A1 | 1/2006 | Funk et al. | |
| 2006/0033038 A1 * | 2/2006 | Moses et al. | 250/440.11 |
| 2006/0231773 A1 | 10/2006 | Katagiri et al. | |
| 2007/0210253 A1 | 9/2007 | Behar et al. | |

FOREIGN PATENT DOCUMENTS

| | | |
|---|---|---|
| WO | WO 89/01698 | 2/1989 |
| WO | WO 2008/050321 | 5/2008 |
| WO | WO 2010/001399 | 1/2010 |
| WO | WO 2010/035265 | 4/2010 |

OTHER PUBLICATIONS

An International Preliminary Report dated Apr. 7, 2011, which issued during the prosecution of Applicant's PCT/IL09/00926.

An International Search Report dated Jan. 26, 2010, which issued during the prosecution of Applicant's PCT/IL09/00926.

A Supplementary European Search Report dated Mar. 6, 2012 which issued during the prosecution of Applicant's European App No. 09815770.

* cited by examiner

FIG. 15     1500

SCANNING ELECTRON MICROSCOPE, AN INTERFACE AND A METHOD FOR OBSERVING AN OBJECT WITHIN A NON-VACUUM ENVIRONMENT

RELATED APPLICATIONS

This application claims priority of U.S. provisional patent Ser. No. 61/077,955, filing date 3 Jul. 2008, U.S. provisional patent Ser. No. 61/077,981, filing date 3 Jul. 2008, U.S. provisional patent Ser. No. 61/077,977, filing date 3 Jul. 2008 and U.S. provisional patent Ser. No. 61/077,970, filing date 3 Jul. 2008, which are incorporated herein by reference.

BACKGROUND OF THE INVENTION

High resolution microscopy is used in research and development, quality assurance and production in diverse fields such as material science, life science, the semiconductor industry and the food industry.

Optical microscopy, dating back to the seventeenth century, has reached a brick wall defined by the wavelength of deep Ultra Violet photons, giving a finest resolution of about 80 nm. The popularity of optical microscopy stems from its relative low price, ease of use and the variety of imaging environmental parameters—all translated to availability.

Scanning electron microscopy provides a much finer resolution (down to a few nanometers), but in order to achieve this high resolution the inspected object must be placed in a vacuum environment.

Determining a Working Distance

In non-vacuum Scanning Electron Microscopes, the distance between the object and the microscope (also referred to as "working distance") is of the order of a few to tens microns. Knowing the exact working distance is important for resolution and contrast optimization, for safe imaging of an object without contacting the optics of the microscope, for reducing contamination generated by such a contact, and for generating a focused image by setting the focusing lens accordingly. There is a growing need to provide a fast and accurate method and system for determining the working distance.

Reducing the Working Distance

The working distance between the object and the optics of the microscope should be as small as possible but large enough to prevent the object from contacting the microscope or otherwise contaminating the microscope. There is a growing need to provide an optimal trade off between the working distance and contamination hazards.

SUMMARY OF THE INVENTION

According to an embodiment of the invention a method is provided. The method is for observing an object that is positioned in a non-vacuum environment, the method includes: generating an electron beam in the vacuum environment; scanning a region of the object with the electron beam while the object is located below an object holder; wherein the scanning comprises allowing the electron beam to pass through an aperture of an aperture array, pass through an ultra thin membrane that seals the aperture, and pass through the object holder; wherein the ultra thin membrane withstands a pressure difference between the vacuum environment and the non-vacuum environment; and detecting particles generated in response to an interaction between the electron beam and the object.

According to an embodiment of the invention a scanning electron microscope is provided. The scanning electron microscope includes: an electron beam source positioned in a vacuum environment; the electron beam source is adapted to generate an electron beam; an interface between the vacuum environment and a non-vacuum environment in which an object is positioned, the interface comprises an aperture array sealed by an ultra thin membrane that is substantially transparent to the electron beam and withstands a pressure difference between the vacuum environment and the non-vacuum environment; an object holder; a scanner that scans a region of the object with the electron beam while the object is located below the object holder; wherein the electron beam passes through an aperture of the aperture array, passes through the ultra thin membrane, and passes through the object holder; and a detector that detects particles generated in response to an interaction between the electron beam and the object.

According to an embodiment of the invention a method is provided. The method is for observing an object that is positioned in a non-vacuum environment, the method includes: illuminating an area of an object with an electron beam; wherein the electron beam is generated in the vacuum environment and passes through an aperture of an aperture array and passes through an ultra thin membrane that seals the aperture; wherein the ultra thin membrane withstands a pressure difference between the vacuum environment and the non-vacuum environment; detecting particles generated in response to an interaction between the electron beam and the object; and determining a distance between the object and the ultra thin membrane in response to detected particles.

According to an embodiment of the invention a scanning electron microscope is provided. The scanning electron microscope includes: an electron beam source positioned in a vacuum environment; the electron beam source is adapted to generate an electron beam; optics configured to direct the electron beam towards an area of the object; an interface between the vacuum environment and a non-vacuum environment in which an object is positioned, the interface comprises an aperture array sealed by an ultra thin membrane that is substantially transparent to the electron beam and withstands a pressure difference between the vacuum environment and the non-vacuum environment; at least one detector that detects particles generated in response to an interaction between the electron beam and the object; and a controller configured to determine a distance between the object and the ultra thin membrane in response to detection signals generated by the at least one detector.

According to an embodiment of the invention a method is provided. The method is for aligning an electron beam and an aperture of an aperture array, the method includes: obtaining an image of a first area of the aperture array; wherein the first area comprises multiple apertures of the aperture array; calculating a spatial relationship between a selected aperture of the multiple apertures and a reference location within the first area; aligning an electron beam with the reference location in response to the spatial relationship; and obtaining an image of a region of an object that is positioned in a non-vacuum environment; wherein the obtaining comprises scanning the region by an electron beam that is generated in a vacuum environment, passes through the selected aperture and passes through an ultra thin membrane that seals the selected aperture; wherein the ultra thin membrane withstands a pressure difference between the vacuum environment and the non-vacuum environment.

According to an embodiment of the invention a scanning electron microscope is provided. The scanning electron microscope includes: an electron beam source positioned in a vacuum environment; the electron beam source is adapted to generate an electron beam; an interface between the vacuum environment and a non-vacuum environment in which an object is positioned, the interface comprises an aperture array sealed by an ultra thin membrane that is substantially transparent to the electron beam and withstands a pressure difference between the vacuum environment and the non-vacuum environment; optics configured to scan, with an electron beam, a first area of the aperture array and scan a second area of the aperture array; wherein the first area comprises multiple apertures of the aperture array; wherein the second area is smaller than the first area and comprises a selected aperture; at least one detector that detects particles generated in response to an interaction between the electron beam and at least one entity out of the interface and the object; and a controller configured to: calculate a spatial relationship between a selected aperture of the multiple apertures and a reference location within the first area; and control an alignment of the electron beam with the reference location in response to the spatial relationship.

DETAILED DESCRIPTION OF THE DRAWINGS

Figure 1:
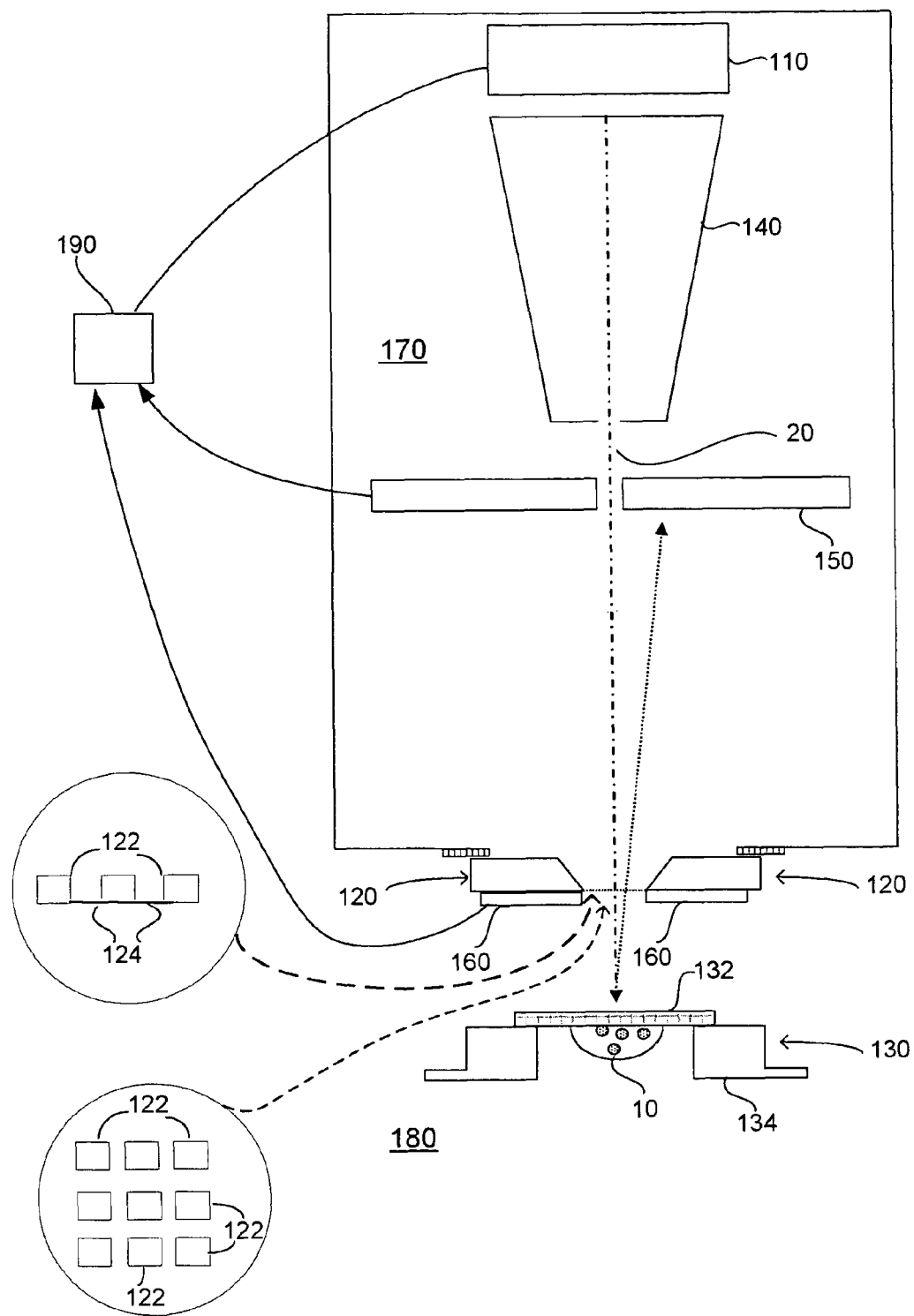
FIG. 1 illustrates a portion of a scanning electron microscope according to an embodiment of the invention.

According to various embodiments of the invention a scanning electron microscope and a method are provided. An object is placed, in a non-vacuumed environment, underneath an object holder that may include at least one partially transparent foil. The foil can be of the types commonly used in transmission electron microscope (TEM) grid, with the object placed onto the side far from the microscope. (It is so-called "inverted"). Alternatively, the object can be placed on top of foil that is then flipped, turned or otherwise inverted.

The object holder may include at least one fully transparent portion, at least one partially transparent portion or a combination thereof.

This configuration allows placing non-solid objects such as gels, liquids, biological cells to be placed such as to contact a lower side of the sample holder and this sample holder can be positioned at small distance from the scanning electron microscope optics (from the interface between a vacuum environment and a non-vacuum environment) thus minimizing the possibility of contact with the scanning electron microscope. This configuration also allows placing objects such as powders, flakes, or particular small crystals.

This so called inverted configuration prevents contamination of the scanning electron microscope optics while providing a small working distance.

The inverted configuration also facilitates having the sample in a separate environment (also referred to as mini-environment) and controlling a temperature of the mini environment, controlling a pressure maintained in the mini environment, controlling a gas composition of the mini environment, providing solvents to the mini environment and applying mechanical stress levels on the object or within the mini environment. The inverted configuration also facilitates the addition of chemicals to the mini environment whether in gas, liquid or solid particles form.

The inverted configuration also allows connecting the sample electrically to testing equipment. The electrical connectors can be connected to the lower part of the object holder or integrated within.

The inverted configuration also allows irradiating the sample with photons by a light source that can be a part of another microscope or inspection tool.

All the manipulations mentioned above in relation to the mini environment can be executed prior to imaging with the electron microscope or during imaging which allows to image changes in real time.

The sample holder can be connected to, or placed on, two or three axes stage (such as a XYZ stage) that can move the object holder and hence move the object for various purposes such as but not limited to alignment with a selected aperture, moving the object to be inspected by another inspection tool or microscope, and the like.

According to an embodiment of the invention the sample holder can be moved (while maintained in a mini-environment) to an imaging or measurement probe or tool located on a different platform or different system.

The object holder can be made of a very thin foil that has minimum impact on the image resolution and contrast. The foil can be transparent both for photons and electrons with typical energies of 5-30 kV.

The object holder is located in the non-vacuum environment and does not need to withstand a pressure gradient between the vacuum environment and the non-vacuum environment—thus simplifying its manufacturing process and expanding the range of materials that can be used.

The foil can also be reinforced with a grid structure which can be placed on either the side facing the electron microscope, the side opposite the electron microscope or on both sides.

The inverted sample holder can be made of multiple compartments enabling putting multiple samples on the same holder for analysis.

The inverted configuration facilitates a scanning of an object that is an electrochemical cell and generating images (in real time) of electrochemical processes for example deposition. One of the electrodes of the electromechanical cell can be shaped as a grid and can be used to support a foil of the object holder. This electrode can be imaged with the scanning electron microscope. Another electrode of the electrochemical cell may contact a solution positioned at a lower part of the electrochemical cell.

The inverted configuration also facilitates connecting the sample to an external electrical power source either having the entire object at a desired potential or connecting more than a single electrode for creating potential differences on the foil.

According to an embodiment of the invention a method is provided. The method may include placing an object such as a non-solid object on a lower side of an object holder such that the object contacts at least one partially transparent portion (such as a foil) of the object holder; imaging the object, while placed on the lower side of the sample holder by at least one scanning electron microscope.

Scanning Electron Microscope

Figure 2:
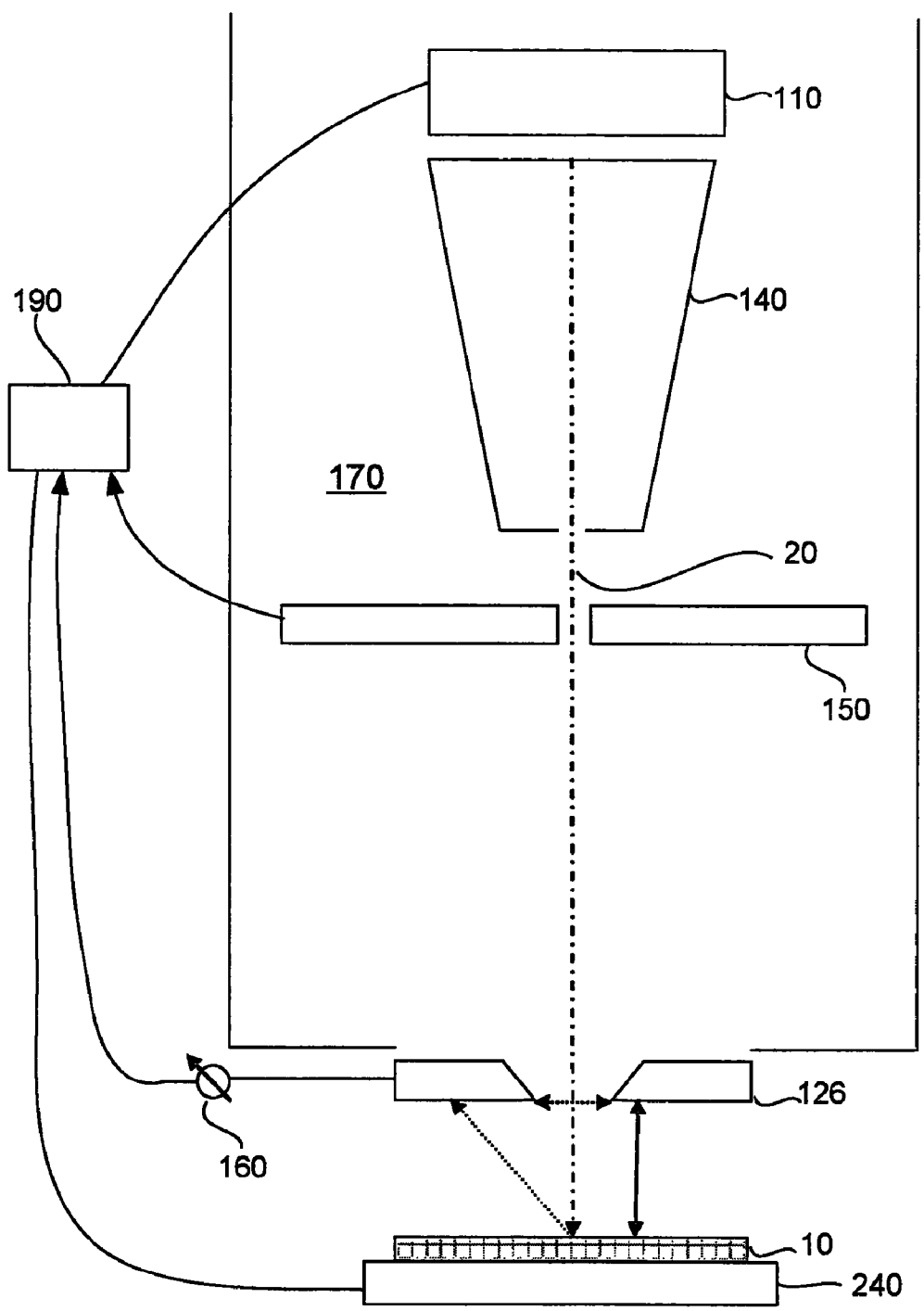
FIG. 2 illustrates a portion of a scanning electron microscope according to another embodiment of the invention.

FIG. 1 illustrates a portion of scanning electron microscope 100 according to an embodiment of the invention. FIG. 2 illustrates a portion of scanning electron microscope 100 according to another embodiment of the invention.

FIG. 1 illustrates an "inverted configuration" of scanning electron microscope 100 while FIG. 2 illustrates a non-inverted configuration of scanning electron microscope 100. It is noted that a scanning electron microscope that can operate in both configurations as well as a scanning electron microscope that can operate at only one of these configurations can be provided without departing from the spirit of the invention.

The inverted configuration allows a reduction of the working distance by placing the object below an object holder—placing the object at a side that does not face the interface between the vacuum and non-vacuum environments.

Scanning electron microscope 100 includes electron beam source 110, interface 120, object holder 130, optics 140, scanner 140 and one or more detectors such as detectors 150 and 160. Scanner 140 is illustrated as including multiple deflection coils 140. It can also include a mechanical stage that can move object holder 130 and therefore object 10.

Electron beam source 110 is positioned in vacuum environment 170. Electron beam source 110 is adapted to generate electron beam 20.

Interface 120 is positioned between vacuum environment 170 and non-vacuum environment 180. Object 10 is positioned in non-vacuum environment 170. Interface 120 includes aperture array 122 that is sealed by an ultra thin membrane 124 that is substantially transparent to electron beam 20 and withstands a pressure difference between vacuum environment 170 and non-vacuum environment 180.

Object holder 130 holds object 10. FIG. 1 illustrates object holder 130 as placed above object 10.

Scanner 140 scans a region of object 10 with electron beam 20 while object 10 is located below object holder 130. Object 10 is below object holder 130 in a sense that it is not placed on an upper part of object holder 130—it does not face the interface 120. Accordingly, electron beam 20 has to pass through object holder 130 or a dedicated portion thereof in order to interact with object 10.

When scanner 140 scans the region of object 10 electron beam 20 passes through one or more apertures of aperture array 122, passes through ultra thin membrane 124, and passes through object holder 130. Object holder 130 can include portions that are transparent or substantially transparent to electron beam 20. Object holder 130 can include a grid that can contact object 10.

Object 10 may be a non-solid object such as fluid, gel, emulsion, biological cell and the like. Object 10 may also be one or more small particles, a powder and the like.

Object 10 may be placed above object holder 130 and object holder 130 can be rotated or otherwise moved or manipulated so that when being scanned by electron beam 20 it is below object holder 130. Alternatively, object 10 may be provided to the lower part of object holder 130 without rotating or otherwise moving object holder 130.

According to an embodiment of the invention object 10 does not contact the lower part of object holder 130 but contacts a gel or emulsion or other non-solid material that contacts object holder 130. Object holder 130 can be shaped to contact a non-solid entity in which the object is inserted. It can include a rigid lower side in order to provide better connectivity to the non-solid entity.

Figure 10:
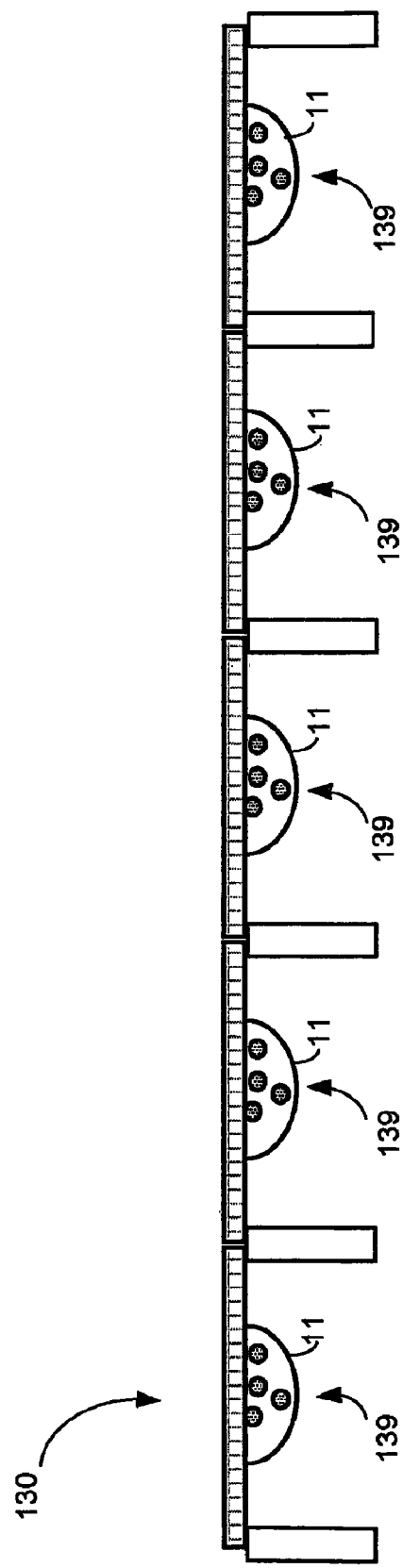
FIG. 10 illustrates an object holder and multiple objects according to an embodiment of the invention.

One or more objects can be located below object holder at a time. Accordingly, object holder 130 can include multiple object holder regions, each region is shaped to contact an object 10. FIG. 10 illustrates object holder 130 as holding multiple objects 11 in multiple regions 139.

Referring back to FIG. 1, each of detectors 150 and 160 detect particles generated in response to an interaction between electron beam 20 and object 10. Detector 150 is located in vacuum environment 170 while detector 160 is located in non-vacuum environment 180.

FIG. 1 illustrates detector 150 as having an aperture through which electron beam 20 passes. It is referred to as "in lens" detector. It can include different detector elements—each capable of generating its own detection signals. Each detector element can also be referred to as a detector.

Detector 160 is positioned in non-vacuum environment 180. It can be connected to interface 120 and measure a current that flows though interface 120. Additionally or alternatively, detector 160 can detect electrons that do not pass through aperture array 122 in other manners.

Scanning electron microscope 100 can be used for various purposes, including but not limited to: (i) image voltage contrast in air; (ii) electron beam lithography on photo resist in air; (iii) high resolution imaging of wafers and processes which are incompatible with vacuum such as a photo resist before curing; (iv) image and analyze wafers and processes which are impacted by the vacuum environment, or wafers and processes which are sensitive to formation of adhesion of a monolayer of contamination molecules; (v) image and analyze large specimen such as solar panels and flat panel display; (vi) image and analyze particles in a solution; (vii) image histology and pathology slides; (viii) image biological cell; (ix) excite X-ray emission for material analysis, whereas an image can be used to find a known location and generate an analysis on an exact location; (x) excite X-ray emission for thickness measurement, whereas an image can be used to find a known location and generate an analysis on an exact location; (xi) excite X-ray emission for density measurement, whereas an image can be used to find a known location and generate an analysis on an exact location; (xii) image and analyze side walls, whereas an image can be used to find a known location and generate an analysis on an exact location, (xiii) image and measure thickness of side walls, whereas an image can be used to find a known location and generate an analysis on an exact location, and the like.

Aperture Array 122 and Ultra Thin Membrane 124

The term aperture array means any arrangement (ordered or non-ordered) of apertures. The apertures of the array can be sealed by one or more ultra thin membranes.

Conveniently, the ultra thin membrane is thinner than a 100 nanometers and is made of low density material such as Carbon or SiN.

When multiple apertures are provided each aperture can be sealed by its own membrane, although this is not necessarily so. A single membrane can seal multiple apertures. According to an embodiment of the invention the membrane can be connected to a very thin grid that defines multiple apertures.

The ultra thin membrane seals an aperture while withstanding the pressure difference between the vacuum environment and the non-vacuum environment.

The ultra thin membrane is used because it has the minimal impact on the electron spot size. For better performance it is advantageous to use higher electron accelerating voltages, preferably 20 kV and higher. Another advantage of using ultra thin membrane is that the electrons used to generate the image can be efficiently collected with detectors situated in the vacuum environment.

The aperture array can include an aperture array of different sized apertures that are sealed by membranes of different areas and thickness. The different apertures can be positioned at the same plane, but this is not necessarily so. For example, apertures and membranes can be positioned in a staggered manner. The apertures positioned at the center of the aperture array can be lower than aperture positioned near the edges of the aperture array. The apertures of the array can be positioned in different planes that are arranged in a symmetrical manner about the center of the aperture array or in relation to a symmetry axis, but this is not necessarily so.

Different apertures can be sealed by ultra thin membranes (or different portions of the same ultra thin membrane) of the same thickness. Alternatively, different apertures can be sealed by ultra thin membranes (or different portions of the same ultra thin membrane) of different thickness.

The thickness can be responsive to the size of the aperture. Larger apertures may be sealed by thicker membranes. Larger apertures provide larger field of view but thicker membranes reduce the resolution. Accordingly, a system that includes membranes of different thickness and apertures of different areas can provide multiple trade-offs between field of views and resolution.

The different apertures can be accessed by moving the apertures to the electron beam position, and/or by deflecting the electron beam. According to another embodiment of the invention an aperture array includes evenly sized apertures and conveniently evenly sized membranes.

The apertures of the aperture array can all have the same shape but this is not necessarily so. Non limiting examples of apertures shapes include circles, ellipse, square, triangle, rectangle, and the like.

An entire area of the object can be imaged by scanning that area by an aperture array. The scanning axis can be parallel a longitudinal axis or a latitudinal axis of the aperture array but can also be oriented in relation to these arrays.

It is noted that when virtually combining the field of view provided by each of the apertures a relatively large (though not continuous) field of view can be obtained. A non-continuous image of sub-areas of the object can be used during navigation stages.

An aperture array can be manufactured in various manners including deposition and etch back. The deposition includes depositing one or more ultra thin membrane on an aperture array. The etch back process includes etching a plate in order to form multiple apertures.

It is noted that different aperture arrays or different aperture can be used in an interchangeable manner. An interface of a scanning electron microscope can include multiple aperture arrays and at a given point of time one (or more) aperture array can be illuminated by one or more electron beams.

Scanner 140

Scanner 140 can scan an area or a region of object 10 by at least one of the following or a combination of both: (i) electrostatic scanning of electron beam 20; (ii) mechanical scanning of the object with electron beam 20 in spot mode to form an image, which can be useful if one utilizes a very small aperture and wants to generate an image with field of view larger than the size of the aperture; (iii) mechanical scanning of the microscope with electron beam 20 in spot mode to form an image which can be useful if one utilizes a very small aperture and wants to generate an image with field of view larger than the size of the aperture; (iv) mechanical scanning of the aperture or window simultaneously with electrostatic scanning of electron beam 20 so that electron beam 20 follows the window position; (v) scanning the aperture by magnetic scanning.

FIG. 1 illustrates scanner 140 as placed between interface 120 and electron beam source 110 but this is not necessarily so. For example—scanner 140 can include a stage (such as stage 240 of FIG. 2) that can move object 10. The stage can be connected to object holder 130 or be a part of object holder 130.

Detectors 150, 160

Particles such as electrons that interact with the object can cause various particles to be scattered or reflected from the object. The interaction can generate secondary electrons, backscattered electrons, characteristic X-rays and in some cases Cathodoluminescence. The Cathodoluminescence can be either a surface property or caused due to light emission from markers or labeling molecules. The emitted signal is detected with the aid of one of the mentioned above detectors.

FIG. 1 illustrates scanning electron microscope 100 as including detector 150 and detector 160. It is noted that scanning electron microscope 100 can include more or less detectors. For example—scanning electron microscope can have more than a single detector within vacuum environment 170 and, additionally or alternatively, have more than a single detector in non-vacuum environment 180.

According to embodiments of the invention, scanning electron microscope 100 can have only vacuum environment detectors or have only non-vacuum environment detectors. A combination of both can also be provided thus one or more detector is positioned in the non-vacuum environment while one or more other detectors are positioned in the vacuum environment.

Locating one or more detector such as vacuum environment detector 150 in vacuum environment 170 can facilitate small and even very small working distances between the object and one or more apertures, thus contribute to the resolution of the image. Placing detectors in the vacuum environment also enables to use detectors that are less compatible with air such as using coatings which easily oxidize.

It is noted that using different detectors can provide more information about the illuminated area of the object and that multiple detectors can be activated simultaneously.

Detectors 150 and 160 can detect the same type of particles. According to another embodiment different detectors of scanning electron microscopes can detect different types of particles.

For example—one detector of scanning electron microscope 100 can detect backscattered electrons (BSE). A BSE detector can be located between ultra thin membrane 124 and an objective lens (not shown) of scanning electron microscope 100. The BSE detector can have an annular shape that defines an opening enabling electron beam 20 to pass. The BSE detector can also be segmented to enhance topography information.

According to another embodiment one detector can detect electrons and another detector detects light. Both detectors may operate simultaneously.

A parabolic mirror (not shown) located between ultra thin membrane 124 and an objective lens of scanning electron microscope 100, having an opening enabling electron beam 20 to pass will collect the light to a photomultiplier placed to the side of the electron path.

Scanning electron microscope 100 can include one or more X-ray detectors that can assist in material analysis. Integrating such analysis to an imaging engine permits localization of the object to be analyzed enabling higher sensitivity for smaller objects as opposed to macroscopic analysis. Another possibility is to use emitted X-rays for image generation which is commonly referred to as X-ray mapping.

For analysis with low resolution where working distance of >100 microns can be applied, an X-ray detector can be located outside the vacuum environment. It would be preferable to use an annular detector to increase the collection efficiency.

For analysis with high resolution, where smaller working distance has to be applied, lets say <100 microns, the detector will be situated inside the vacuum. If a side detector is used it can be in a configuration where backscattered electrons, secondary electrons and light can be detected. An alternative arrangement where emphasis is on high X-ray collection efficiency is to use an annular X-ray detector such as a multi cell Silicon drift detector (SDD) manufactured by PN Sensor, Germany.

Vacuum Environment 170

A scanning electron microscope column can operate under vacuum. The column of scanning electron microscope 100 can include multiple differentially pumped spaces that are separated by a non-sealed aperture. It is noted that the sealing provided by interface 120 can render such a partition unnecessary. It is noted that the vacuum of vacuum environment 170 can be provided by one or more pumps such as an ion pump, a turbo pump and the like. Since the system is isolated a microscope can be designed without a pump as done in a CRT.

Non-Vacuum Environment 180

The environment between the sample and the column can be of any composition. In particular, it can be filled with air, at least partially filled with nitrogen or dry nitrogen where the efficiency of light emission due to secondary gas excitation is high because the oxygen which is a quencher of this process is absent. Non-vacuum environment 180 can be at least partially filled with inert gases and in particular He or mixture of He where the mean free path of the electron is higher improving the signal to noise at larger working distances.

Inverted Configuration

Figure 3:
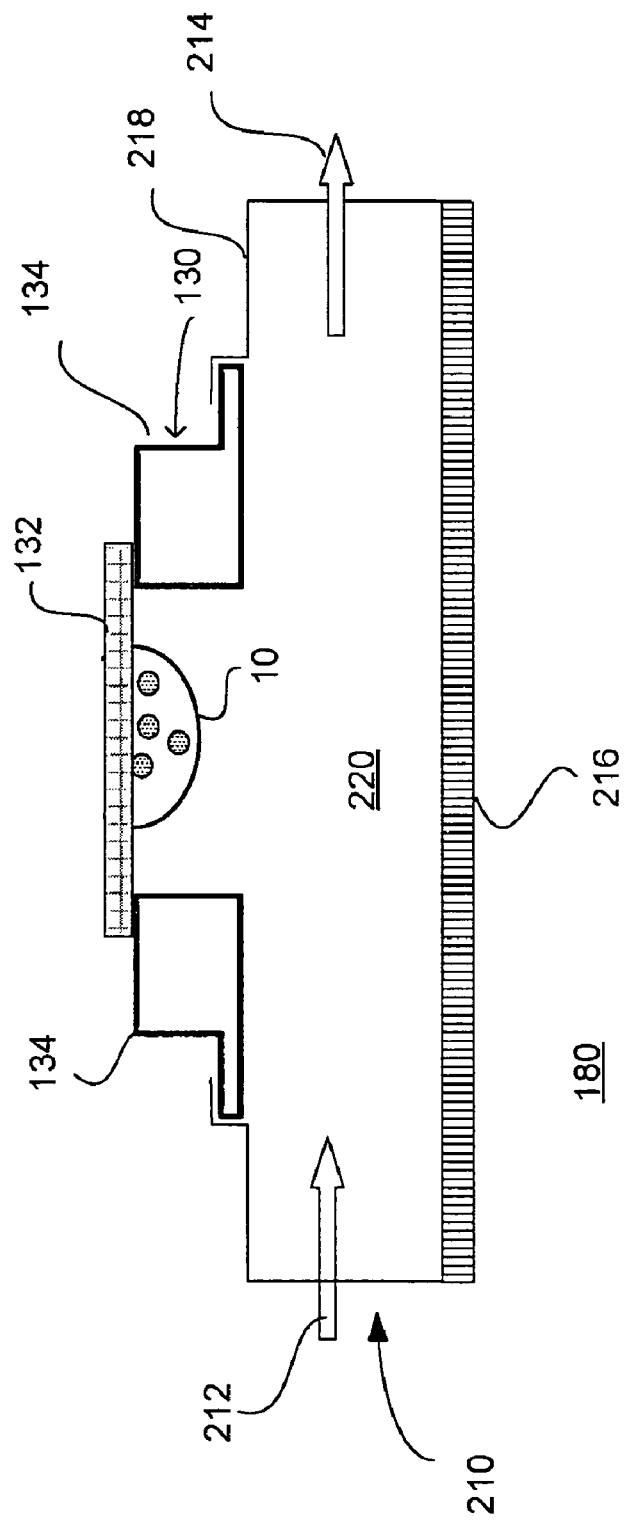
FIG. 3 illustrates an object, a sample holder, non-vacuum environment and a chamber according to an embodiment of the invention.

FIG. 3 illustrates object 10, sample holder 130, non-vacuum environment 180 and chamber 210 according to an embodiment of the invention.

Chamber (also referred to as micro-chamber) 210 can define a space in which mini environment 220 can exist. Mini environment 220 is defined around object 10. Mini environment 220 is smaller than non-vacuum environment 180 and may be even much smaller. For example it can be 5%, 10%, 20% or 30% of the non-vacuum environment, but this is not necessarily so.

Chamber 210 can control one or more characteristics of mini environment 220 by introducing one or more chemicals, by heating or cooling mini environment 220, by drying of introducing vapors such as to determine a humidity of mini environment 220, by directing radiation towards object 10, by applying force (for example squeezing object 10 against object holder 130), and the like.

Chamber 210 includes frame 218, inlet 212, outlet 214, temperature affecting element 216 (such as a cooling element, a heating element or both). Inlet 212 can be used to inject one or more chemicals, gases, fluids and the like.

FIG. 3 illustrates sample holder 130 as including a transparent portion 132 (such as a semi transparent film) and sample holder base 134. Object 10 is positioned below transparent portion 132.

Figure 4:
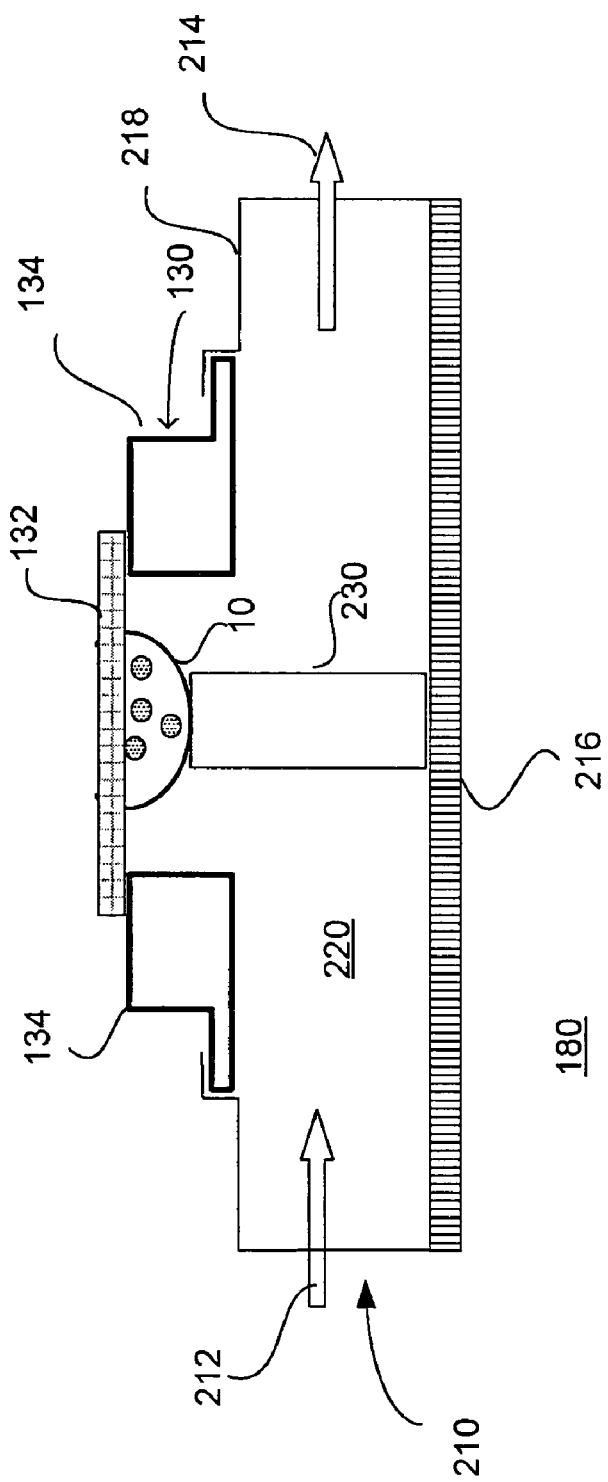
FIG. 4 illustrates a chamber that includes a force applying component according to an embodiment of the invention.

FIG. 4 illustrates chamber 210 that includes force applying component 230 according to an embodiment of the invention. Force applying component 230 can apply force on object 10 while object 10 is within mini environment 220. It is noted that scanning electron microscope 100 can include a force applying component even without having chamber 210.

Figure 5:
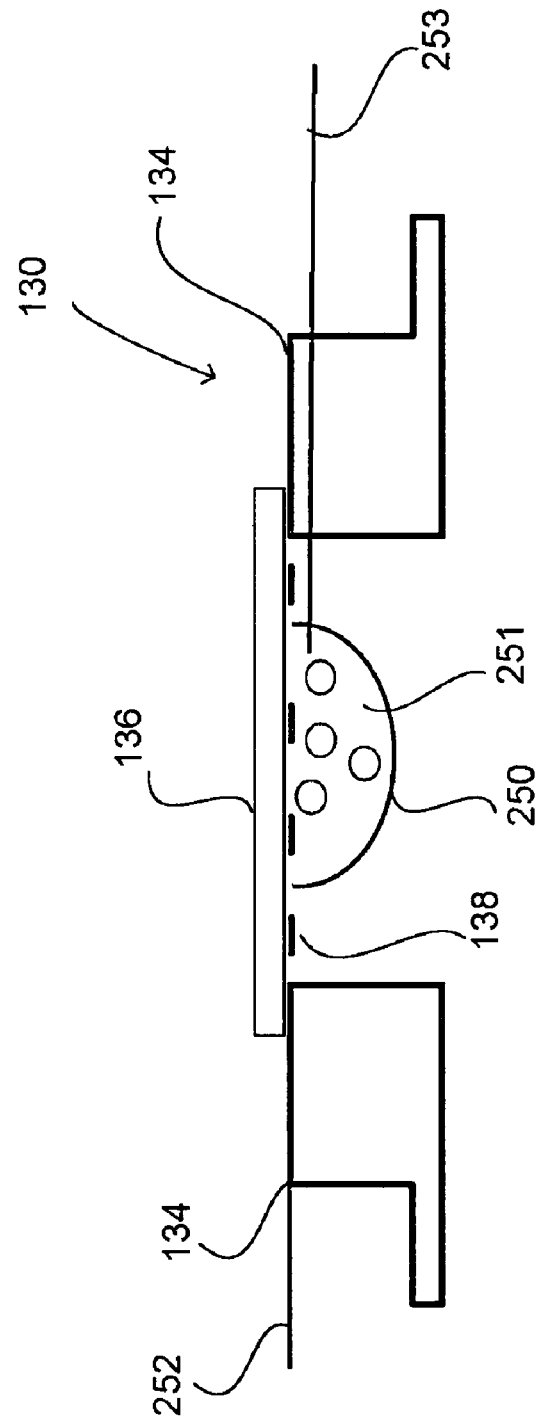
FIG. 5 is a cross section of an object that is an electrochemical cell and of a sample holder according to an embodiment of the invention.

FIG. 5 is a cross section of an object 10 that is an electrochemical cell 250 and of sample holder 130 according to an embodiment of the invention.

Electromechanical cell 250 includes electrolyte solution 251 that contacts semi transparent film 136 of sample holder 130 that in turn is supported by conducting grid 138. Conducting grid 138 serves as one of the electrodes of electromechanical cell 250 and can be electrically coupled (via connector 252) to an electrical device (not shown). Second electrode 253 of electrochemical cell 250 can contact electrolyte solution 251. Sample holder base 134 can be made of an insulating material.

Figure 6:
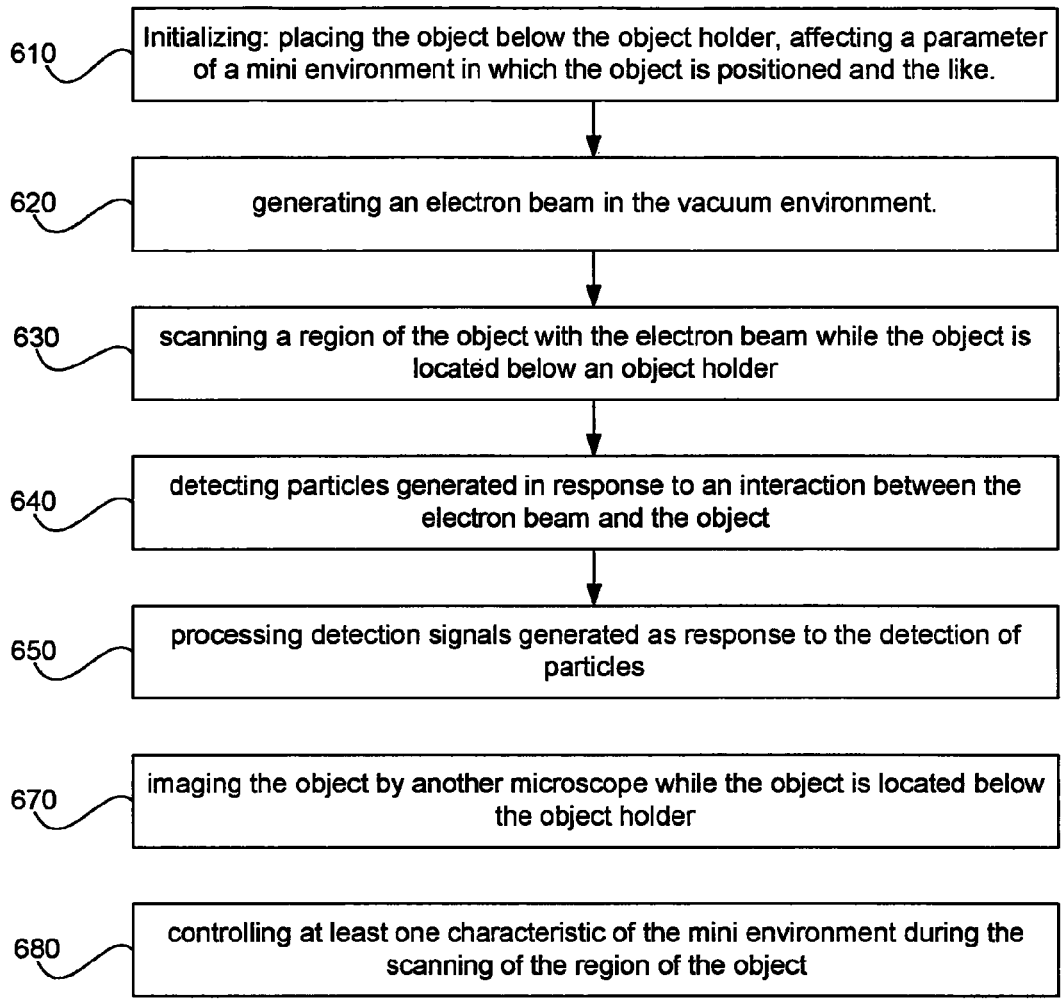
FIG. 6 illustrates a method for observing an object that is positioned in a non-vacuum environment, according to an embodiment of the invention.

FIG. 6 illustrates method 600 for observing an object that is positioned in a non-vacuum environment, according to an embodiment of the invention.

Method 600 may start by initializing stage 610. Stage 610 can include placing the object below the object holder, affecting a parameter of a mini environment in which the object is positioned and the like:

Stage 610 can include placing the object such as to contact a lower side of the object holder, placing the object such as to contact a foil of the object holder, placing the object on the object holder and than rotating or otherwise manipulating the object holder so that the object is placed below the object holder.

Stage 610 can include placing the object within a non-solid entity that contacts a lower side of the object holder and scanning a region of the object.

Stage 610 may include placing multiple objects below the object holder.

Stage 610 may include imaging the object by a low magnification technique such as optical microscope to facilitate navigation to the object. Alternatively, stage 610 can include navigating to the object in response to an image of the object (or object vicinity) that may be acquired by applying an imaging process that differs (at least by its resolution) from the imaging process that is executed during stages 630-650.

Stage 610 is followed by stage 620 of generating an electron beam in the vacuum environment. Stage 620 can include generating multiple electron beams.

Stage 620 is followed by stage 630 of scanning a region of the object with the electron beam while the object is located below an object holder. Stage 630 of scanning includes allowing the electron beam to pass through an aperture of an aperture array, pass through an ultra thin membrane that seals the aperture, and pass through the object holder. The ultra thin membrane withstands a pressure difference between the vacuum environment and the non-vacuum environment.

Stage 630 can include scanning one or more regions of one or more objects by one or more electron beams.

Stage 630 may include at least one of the following or a combination thereof: (i) scanning at least one region of the object by deflecting the at least one electron beam and introducing a corresponding mechanical movement of the aperture array; (ii) scanning at least one region of the object by deflecting the at least one electron beam and introducing a corresponding mechanical movement of the aperture array; wherein a component that includes the aperture array is flexibly connected to another component of an interface that separates the vacuum environment from the non-vacuum environment; (iii) scanning multiple regions of the object by deflecting the at least one electron beam that pass through multiple apertures of the aperture array; (iv) scanning multiple regions of the object by deflecting the at least one electron beam that pass through multiple apertures of the aperture array and introducing a corresponding mechanical movement of the aperture array; (v) scanning a region of the object by deflecting the at least one electron beam by a deflector positioned within the vacuum environment.

Stage 630 is followed by stage 640 of detecting particles generated in response to an interaction between the electron beam and the object.

Stage 640 is followed by stage 650 of processing detection signals generated as response to the detection of particles. Stage 650 can include generating an image of the region of the object, determining a state of the object, or evaluating other parameters of the object. The processing can be preceded by, followed by or executed in parallel of storing the detection signals.

Figure 25:
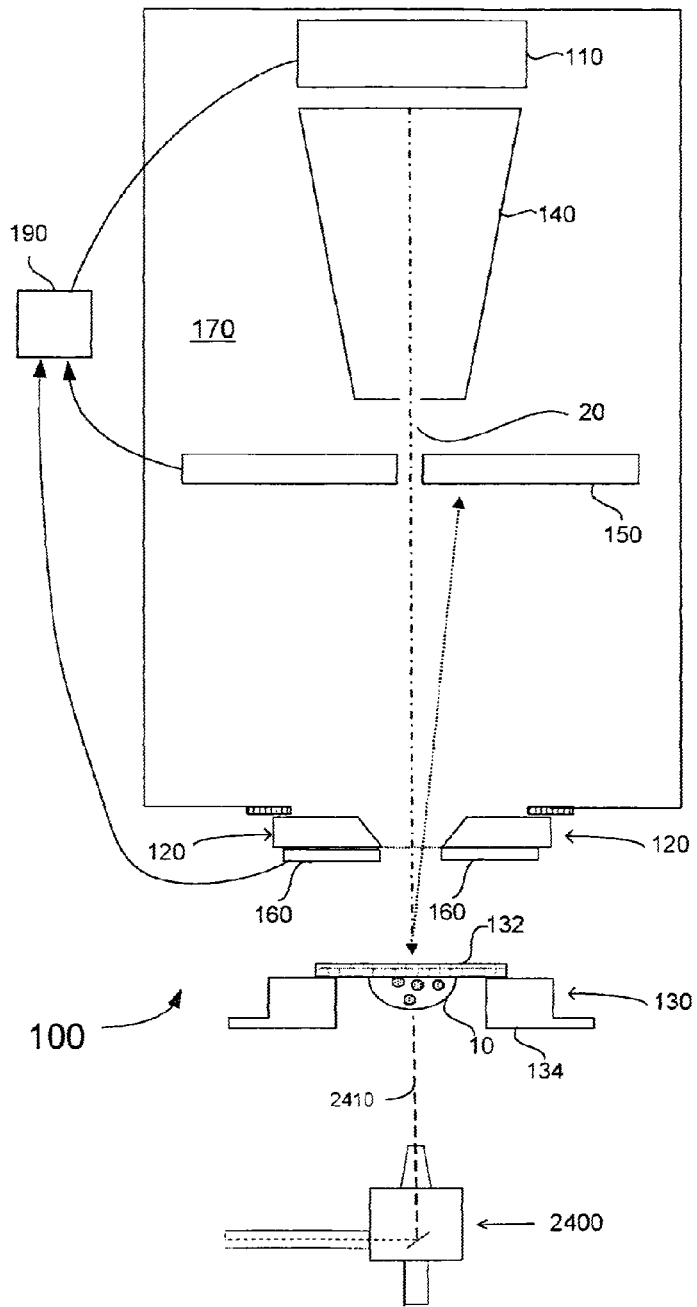
FIG. 25 illustrates a scanning electron microscope and another microscope according to an embodiment of the invention.

According to an embodiment of the invention method 600 includes stage 670 of imaging the object by another microscope while the object is located below the object holder. The other microscope can be an optical tool that directs light towards the lower part of the object. FIG. 25 illustrates another microscope such as optical microscope 2400 that images object 10 while object is located below object holder 130. Optical microscope 2400 directs a light beam 2410 that propagates along an optical axis that is normal to object 10—as illustrated by dashed line 2410. FIG. 25 illustrates optical microscope 2400 and scanning electron microscope 100 as having optical axes that are opposite to each other. It is noted that the optical axis of these microscopes can be oriented in relation to each other by angles that may differ from 180 degrees. Both microscopes 100 and 2400 can image or scan object simultaneously, in a partially overlapping manner or in a non-overlapping manner in which each microscope images or scans object 10 during non-overlapping periods.

Stage 610 can include placing the object within a chamber that defined a mini environment that at least partially surrounds the object. Stage 600 can include stage 680 of controlling at least one characteristic of the mini environment during the scanning of the region of the object. The controlling can include inducing at least one chemical within the mini environment, applying force on the object while the object is scanned, changing a temperature of the mini environment, changing a humidity of the mini environment, and the like.

Alignment of Electron Beam 20

Referring back to FIG. 1, each of detectors 150 and 160 can send detection signals that may be processed by controller 190 in order to generate an image of the area of object 10.

An area of the object can be scanned by directing electron beam 20 through a selected aperture of aperture array 122. It can be beneficial to align electron beam 20 with the selected aperture (denoted 123).

Figure 7:
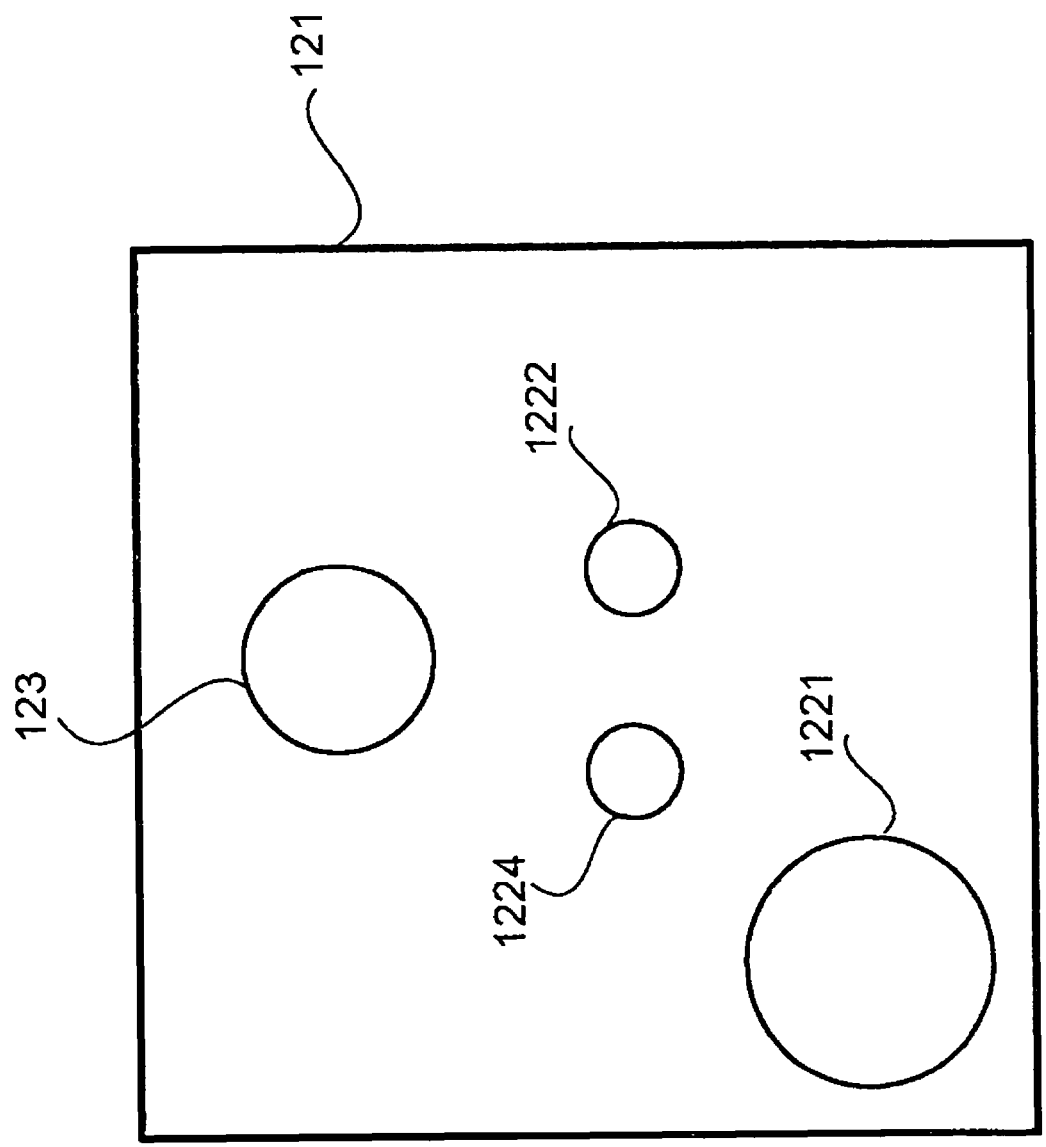
FIGS. 7 and 8 illustrate a first area of an aperture array according to embodiments of the invention.
Figure 8:
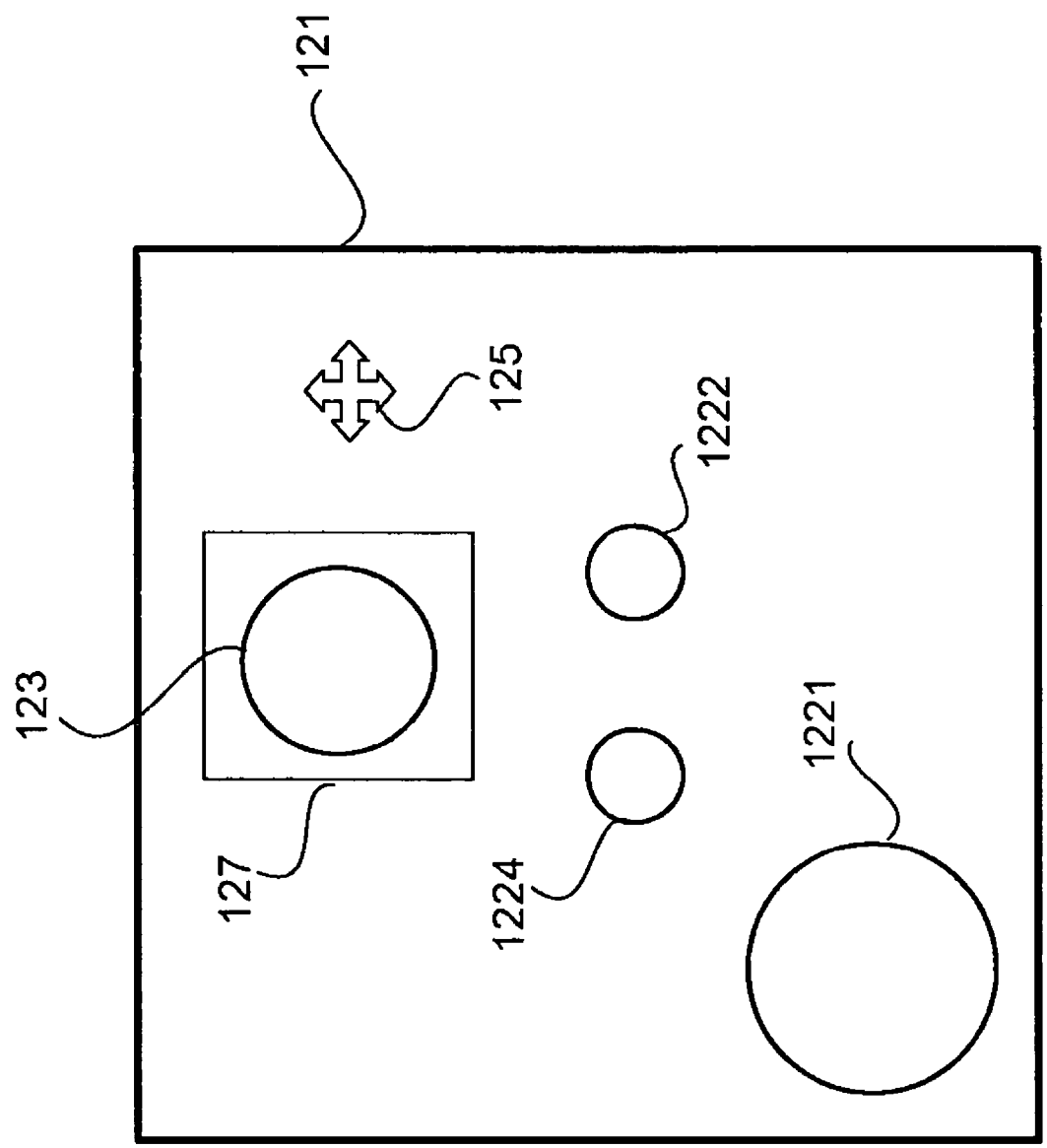

FIGS. 7 and 8 illustrate first area 121 of aperture array 122 according to embodiments of the invention. First area 121 includes apertures 1221, 1222, 123 and 1224. FIG. 8 illustrates first area 121 as further including alignment target 125.

The alignment process can start by scanning with electron beam 20 first area 121 of aperture array 122. First area 121 includes multiple apertures of aperture array 122. First area defines a first field of view of scanning electron microscope. A second field of view of scanning microscope can be defined when the object 10 is scanned through a selected aperture 123.

A detector, such as detector 150 or 160, detects particles generated in response to an interaction between electron beam 20 and first area 121 and sends detection signals to controller 190. Controller 190 may process the detection signals to provide an image of first area 121 and to calculate a spatial relationship (distance, relative angle) between selected aperture 123 and a reference location within first area 121. The reference location can be an alignment target 125, a corner of first area 121, an aperture that has a unique shape and the like.

Once the spatial distance is calculated controller 190 can control a completion of the alignment process. The controller 190 can send control signals to deflectors, to a mechanical unit that can introduce a mechanical movement between interface 120 and scanner 140, and the like. Once the alignment process ends the scanning electron microscope 100 can obtain an image of an area of object 10. The area can include the entire object 10, a small portion of the object or a large area of object 10. The area of object 10 is scanned by scanning a second area 127 of aperture array 122. Second area 127 is smaller than first area 121 and can correspond to selected aperture 123.

The alignment can be done by scanner 140 but can also be done by using mechanical movements. The alignment can utilize at least one of the following: (i) alignment coils ensuring that the one or more electron beams are aligned with the one or more apertures; (ii) mechanical movement of the aperture array (or at least the one or more relevant apertures); and (iii) mechanical movement of the objective or a permanent magnet relative to the aperture array. The advantage is that the moving part is not part of the vacuum sealing.

The mechanical movement of aperture array 122 (or relevant apertures) can be achieved by using a flexible connector between the aperture array and another part of the interface. The flexible connector can be moved by a motor (piezomotor, linear motor and the like).

Either one of the alignment methods mentioned above or combination of one or more alignment methods can be used also to select one or more apertures of an aperture array.

In case of mechanical alignment of the aperture, the movement can be motorized, controlled by a controller and positions can be calibrated or preset to allow seamless work.

A flexible connector can be also used to connect aperture array 122 to frame 126 of FIG. 1. The flexible connector can control the distance between the object and the aperture by moving the aperture array 122 in the direction perpendicular to the plane of object 10. This has the advantage of maintaining a fixed distance between the object and the aperture while moving a small mass.

Figure 9:
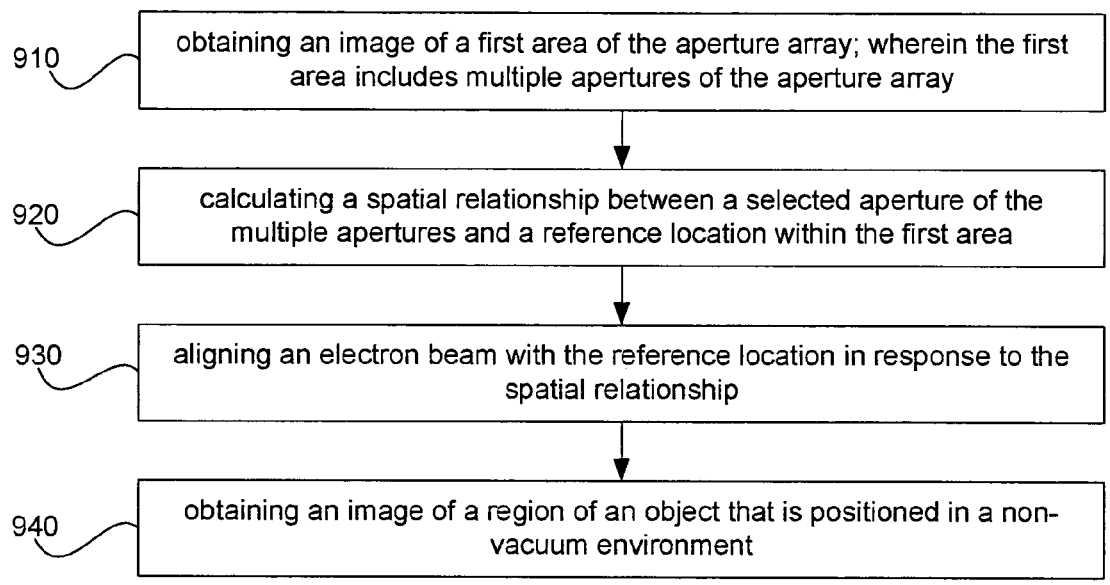
FIG. 9 illustrates a method for aligning an electron beam and an aperture of an aperture array, according to an embodiment of the invention.

FIG. 9 illustrates method 900 for aligning an electron beam and an aperture of an aperture array, according to an embodiment of the invention.

Method 900 starts by stage 910 of obtaining an image of a first area of the aperture array; wherein the first area includes multiple apertures of the aperture array. The first area can include the entire aperture array or a portion thereof. The first are can be selected such as to include a selected aperture and at least one other aperture or reference location.

Stage 910 is followed by stage 920 of calculating a spatial relationship between a selected aperture of the multiple apertures and a reference location within the first area. The reference location can be an alignment target or any other unique point within first area.

Stage 920 is followed by stage 930 of aligning an electron beam with the reference location in response to the spatial relationship.

At the end of stages 920-930 an alignment is achieved. Once such an alignment is achieved method 900 can proceed to obtaining an image of a region of an object. Stage 930 can include applying any of the mentioned above alignment techniques.

Stage 930 is followed by stage 940 of obtaining an image of a region of an object that is positioned in a non-vacuum environment. Stage 940 includes scanning the region by an electron beam that is generated in a vacuum environment, passes through the selected aperture and passes through an ultra thin membrane that seals the selected aperture. The ultra thin membrane withstands a pressure difference between the vacuum environment and the non-vacuum environment.

Stage 940 may includes scanning a second area of the aperture array. The second area is smaller than the first area.

Working Distance

Referring back to FIG. 1, scanning electron microscope 100 can determine the working distance (defined between object 10 and interface 120 or any part thereof) by evaluating the relationship between two or three elements out of: (i) an amount of electrons generated by an interaction between an object and the electron beam; (ii) an amount of electrons that pass through the aperture array; (iii) an amount of electrons that do not pass the aperture array but hit the frame that supports the aperture array.

It is noted that these amount can be measured or estimated in various manners. For example, the amount of electrons that pass through aperture array 122 can be estimated by measuring an amount of electrons that are detected by one or more detectors (such as detector 150) located in vacuumed environment 170. Yet for another example, the amount of electrons that do not pass through aperture array 122 can be estimated by measuring an amount of electrons that impinge on aperture array 122 or on frame 126 that at least partially surrounds aperture array 122. The overall amount of electrons can be estimated by measuring the intensity of electron beam 20 and by estimating the yield of object 10—the yield being the percentage of electrons that are scattered or reflected from object 10. This evaluation can involve illuminating a target of known characteristics (for example—of known yield) and measuring electrons that are emitted from the target, electrons scattered from the target or current that flows through the target.

Each relationship between the mentioned above amounts of electrons reflects the angular distribution of electrons and this angular distribution is responsive to the working distance. Each working distance may be characterized by a unique relationship between the mentioned above amounts of electrons.

Controller 190 may determine the distance by at least one of the following manners or combination thereof: (i) in response to a comparison between detection signals generated when the electron beam is positioned in different locations in relation to the aperture; (ii) in response to a comparison between detection signals generated when the electron beam illuminates the object at different illumination paths; (iii) in response to a comparison between shadows that appear in different locations of an image of the area of the object; (iv) by finding a saturation point; and (v) in response to a size of the aperture and in response to a saturation point; wherein the size of the aperture is set by a shutter.

Figure 24:
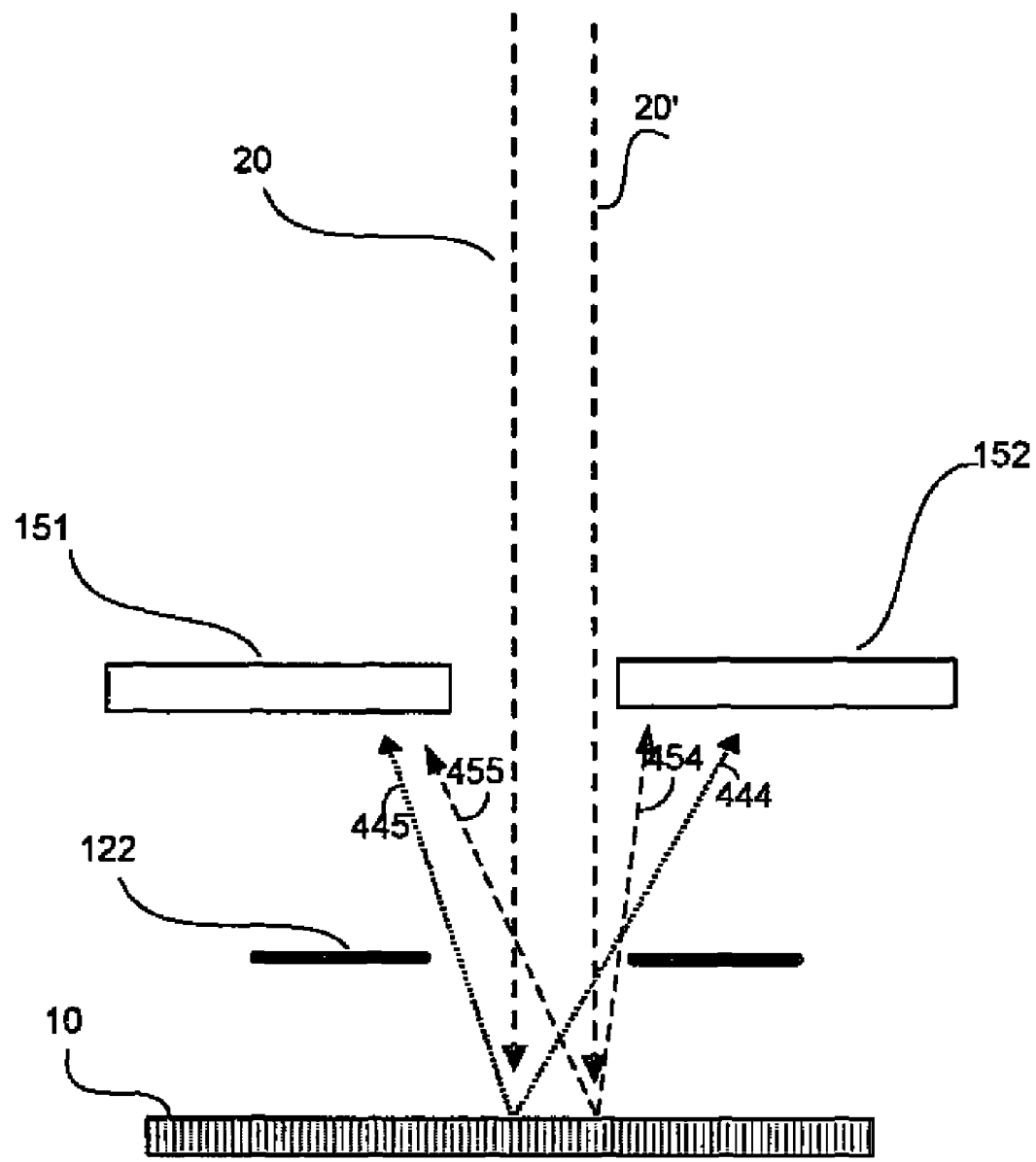
FIG. 24 illustrates on-axis and off-axis illumination according to an embodiment of the invention.

Another to various embodiments of the invention the working distance can be determined in response to a change of the collection angle for different parts of the window. FIG. 24 illustrates electron beam 20 that is positioned at the center of aperture 122 and electron beam 20' that is positioned near the right side of aperture 122. Electron beam 20 causes particles 445 to impinge on a first detection portion 151 and particles 444 to impinge on second detector portion 152. Electron beam 20' causes particles 455 to impinge on a first detection portion 151 and particles 454 to impinge on second detector portion 152.

The available collection angle of particles associated with electron beam 20 is larger that the available collection angle associated with electron beam 20'. This difference is larger for longer working distances and can be manifested in shading of the image near the edges of aperture 122. The dependence of the width of the shading as a function of working distance for a given window geometry can be found either by simulation or calibration. For the measurement itself one can use either discrete points, a line scan crossing the entire window or the entire image.

Figure 11:
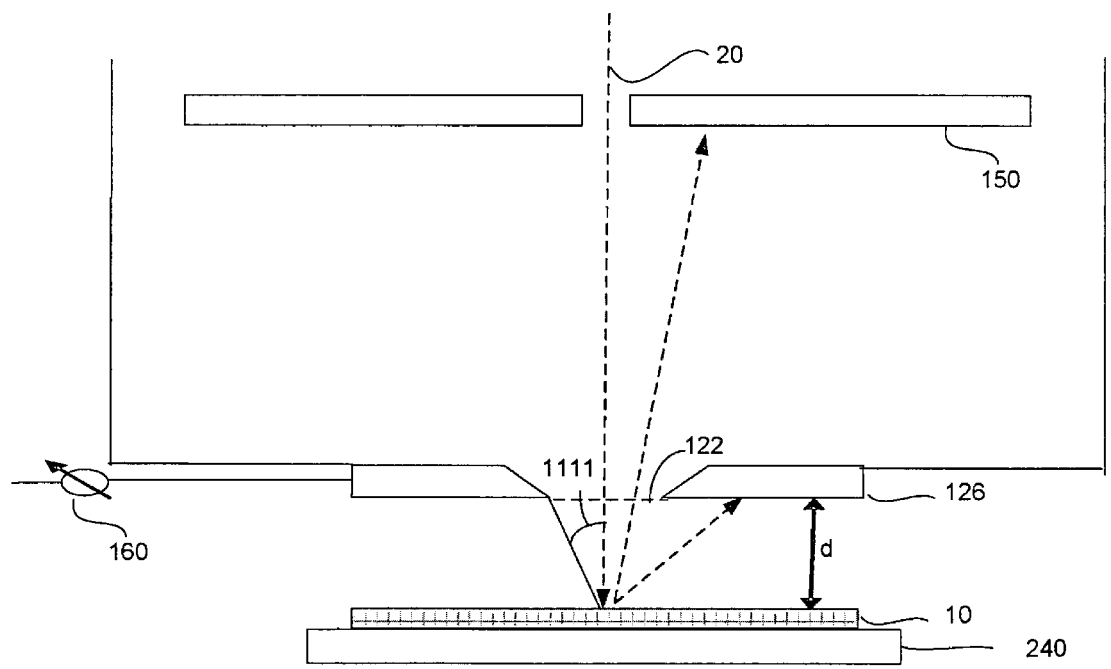
FIG. 11 illustrates a portion of a scanning electron microscope and various particles according to an embodiment of the invention.

FIG. 11 illustrates a portion of scanning electron microscope 100 and various particles according to an embodiment of the invention.

FIG. 11 illustrates detector 160 as a current meter that measures the current that flows through frame 126 that is connected to aperture array 126. FIG. 11 also illustrates electrons that pass through aperture array 122 and are detected by detector 150. FIG. 126 also illustrates a collection angle 1111.

If, for example, the aperture array includes a single circular aperture that has a radius of r, and the working distance is d then the electrons that will pass through this aperture are within collection angle 1111 (defined in relation to a propagation axis of electron beam 20) that equals arctangent(r/d).

Electrons that are outside this angle will hit frame 126. The collection angle is also referred to as solid angle.

If the working distance is large enough then the relationship between electrons that pass aperture array 122 and those who do not pass it are dependent upon the collection angle and are not substantially affected by the shape of frame 126. On the other hand, at relatively small working distances the shape of frame 126 and especially a slope (if such exists) of the inner edges of frame 126 may affect the relationship between the amount of electrons that pass through aperture array 122 and those who does not pass it.

The distribution of particles emitted as a result of an interaction with object 10 can be known in advance and this distribution can assist, once the relationship between the amounts of electrons is measured, to determine the working distance. For example, back scattered electrons are emitted from object 10 with a Lambert (cos θ) distribution, wherein θ is the angle between the emitted electron and the normal to object 10. The calculation of working distance d can also be responsive to known losses.

Table 1 illustrates a relationship between working distances (expresses as multiplication of radius r of a circular aperture), collection angle, percent of electron that pass through the aperture array, percent of electron that do not pass through the aperture array, ratio of electrons that pass aperture array and those who do not pass through the aperture array, and contrast. The contrast is the ratio between the difference and the average of two measurements taken at two working distances separated by r/2.

In a non-limiting example, if the aperture has a radius of 10 microns, the working distances span is 5 to 100 microns

| working distance (window radius) | collection angle (radians) | % electrons that pass through aperture array | % of electrons that do not pass aperture array | Ratio of electrons that pass aperture array and those who do not pass | contrast |
|---|---|---|---|---|---|
| 0.5 | 1.107 | 0.894 | 0.106 | 8.472 | |
| 1 | 0.785 | 0.707 | 0.293 | 2.414 | 1.11 |
| 1.5 | 0.588 | 0.555 | 0.445 | 1.246 | 0.64 |
| 2 | 0.464 | 0.447 | 0.553 | 0.809 | 0.43 |
| 2.5 | 0.381 | 0.371 | 0.629 | 0.591 | 0.31 |
| 3 | 0.322 | 0.316 | 0.684 | 0.462 | 0.24 |
| 3.5 | 0.278 | 0.275 | 0.725 | 0.379 | 0.20 |
| 4 | 0.245 | 0.243 | 0.757 | 0.320 | 0.17 |
| 4.5 | 0.219 | 0.217 | 0.783 | 0.277 | 0.14 |
| 5 | 0.197 | 0.196 | 0.804 | 0.244 | 0.13 |
| 5.5 | 0.180 | 0.179 | 0.821 | 0.218 | 0.11 |
| 6 | 0.165 | 0.164 | 0.836 | 0.197 | 0.10 |
| 6.5 | 0.153 | 0.152 | 0.848 | 0.179 | 0.09 |
| 7 | 0.142 | 0.141 | 0.859 | 0.165 | 0.08 |
| 7.5 | 0.133 | 0.132 | 0.868 | 0.152 | 0.08 |
| 8 | 0.124 | 0.124 | 0.876 | 0.142 | 0.07 |
| 8.5 | 0.117 | 0.117 | 0.883 | 0.132 | 0.07 |
| 9 | 0.111 | 0.110 | 0.890 | 0.124 | 0.06 |
| 9.5 | 0.105 | 0.105 | 0.895 | 0.117 | 0.06 |
| 10 | 0.100 | 0.100 | 0.900 | 0.110 | 0.06 |

Figure 12:
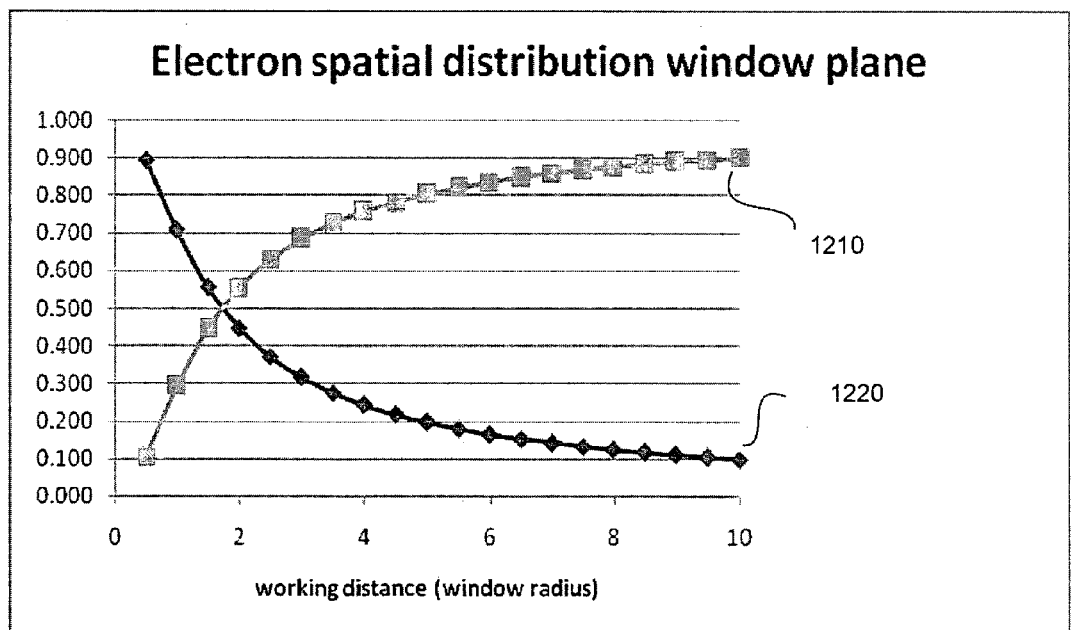
FIG. 12 illustrates a relationship between working distance and electron distribution according to an embodiment of the invention.

FIG. 12 illustrates a relationship between the working distance and electron distribution according to an embodiment of the invention. Curve 1210 illustrates the relative amount (fraction) of electrons that do not pass through aperture array 122 while curve 1220 illustrates the relative amount (fraction) of electrons that pass through aperture array 122.

Figure 13:
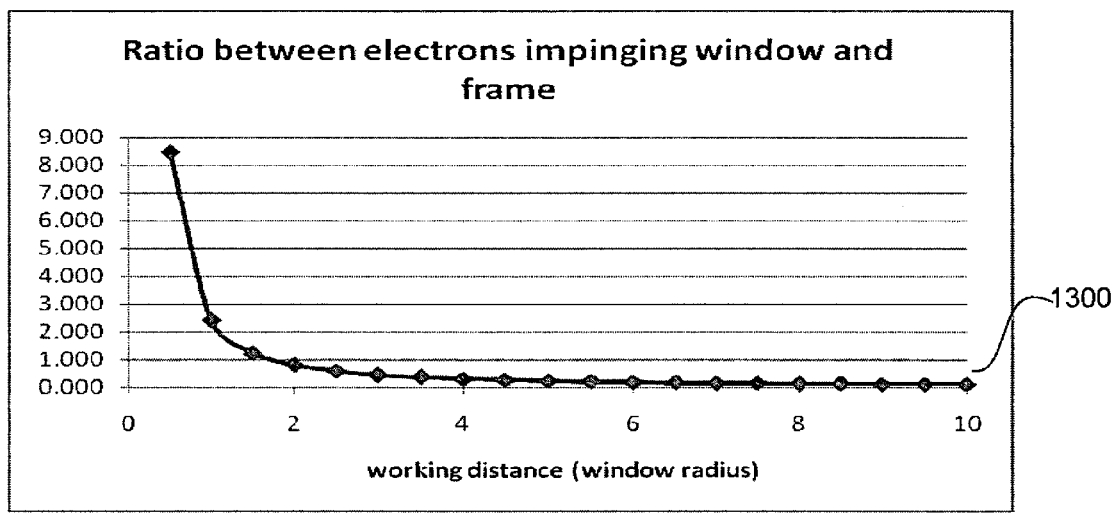
FIG. 13 illustrates a ratio between the fraction of electrons that do not pass through an aperture array and the fraction of electrons that pass through the aperture array, according to an embodiment of the invention.

FIG. 13 illustrates a ratio between the fraction of electrons that do not pass through aperture array and the fraction of electrons that pass through aperture array 122, according to an embodiment of the invention. FIG. 13 includes curve 1300 that illustrated this ratio.

Figure 14:
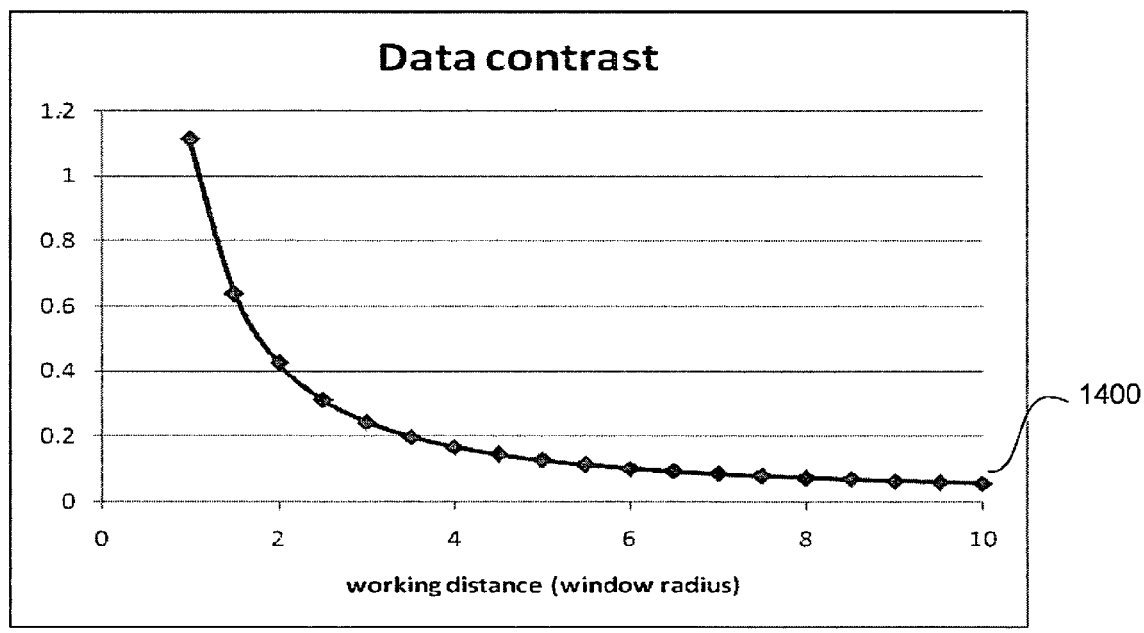
FIG. 14 illustrates a contrast, according to an embodiment of the invention.

FIG. 14 illustrates a contrast; according to an embodiment of the invention. FIG. 14 includes curve 1400 that illustrated the contrast.

Figure 15:
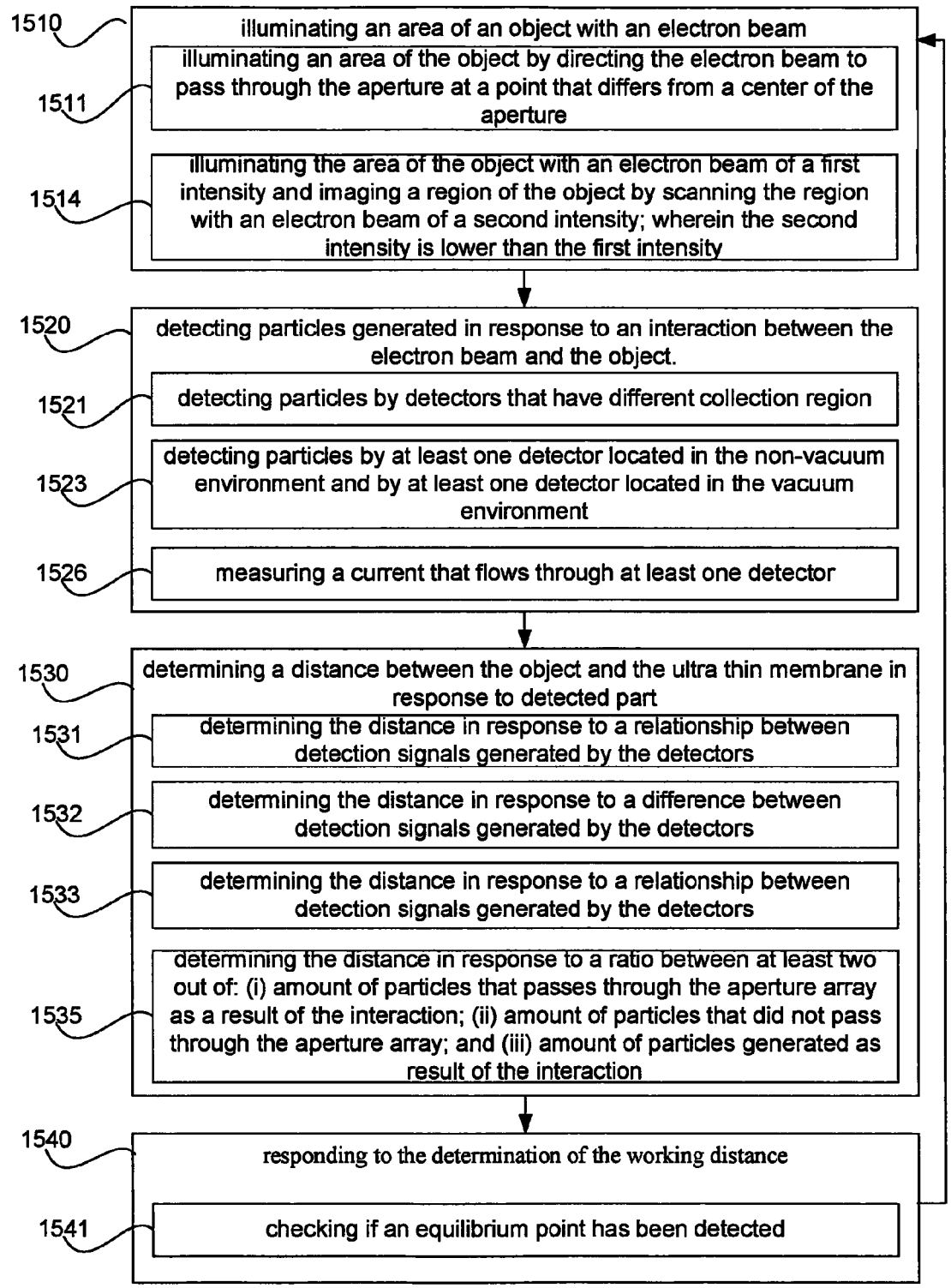
FIG. 15 illustrates a method for observing an object that is positioned in a non-vacuum environment, according to an embodiment of the invention.

FIG. 15 illustrates method 1500 for observing an object that is positioned in a non-vacuum environment, according to an embodiment of the invention.

Method 1500 starts by stage 1510 of illuminating an area of an object with an electron beam. The electron beam is generated in the vacuum environment and passes through an aperture of an aperture array and passes through an ultra thin membrane that seals the aperture. The ultra thin membrane withstands a pressure difference between the vacuum environment and the non-vacuum environment.

Stage 1510 is followed by stage 1520 of detecting particles generated in response to an interaction between the electron beam and the object.

Stage 1520 can include at least one of the following stages or a combination thereof: (i) detecting electrons generated in response to the interaction between the at least one electron beam and the object; (ii) detecting photons generated in response to the interaction between the at least one electron beam and the object; (iii) detecting X-ray emission generated in response to the interaction between the at least one electron beam and the object; (iv) detecting particles by a detector positioned within the vacuum environment; (v) detecting particles by a detector positioned within the non-vacuum environment; (vi) detecting electron current generated as a result of the interaction; and (vii) detecting Cathodoluminescence of the object, fluorescence markers or light emitted due to electron excitation of gas molecules.

Stage 1520 is followed by stage 1530 of determining a distance between the object and the ultra thin membrane in response to detected particles. It is noted that the distance can be determined by an approach curve generated by several measurements at different working distances or by detection signals obtained while the distance between the scanning electron microscope and the object remains the same.

Stage 1530 is followed by stage 1540 of responding to the determination of the working distance. Stage 1540 can include adjusting a focus of the scanning electron microscope to comply with the working distance, changing the working distance in order to achieve a desired working distance, or perform another iteration of stages 1510-1530. The additional iteration can be performed in order to increase the reliability of the determination of the working distance.

Stage 1540 can include changing the working distance and jumping to stage 1510. Thus additional iteration of the measurement process can be performed. This can assist in finding a saturation point or in determining the working distance—especially if only a single detector detects particles during stage 1520.

Accordingly, stage 1540 can include altering the working distance and jumping to stage 1510 until a relationship between particles that pass through the aperture array and particles that not pass through the aperture array maintains constant despite the altering of the distance. This is illustrated by stage 1541 of checking if a saturation point has been detected.

The additional iteration can be executed after changing the working distance but this is not necessarily so. The additional iteration can assist in determining the working distance Stage 1510 can include stage 1511 of illuminating an area of the object by directing the electron beam to pass through the aperture at a point that differs, from a center of the aperture. In this case stage 1520 can include stage 1521 of detecting particles by detectors that have different collection regions and stage 1530 can include stage 1531 of determining the distance in response to a relationship between detection signals generated by the detectors.

Stage 1530 can include stage 1532 of determining the distance in response to a difference between detection signals generated by the detectors.

Stage 1520 can include stage 1523 of detecting particles by at least one detector located in the non-vacuum environment and by at least one detector located in the vacuum environment and stage 1530 can include stage 1533 of determining the distance in response to a relationship between detection signals generated by the detectors.

Stage 1510 can include stage 1514 of illuminating the area of the object with an electron beam of a first intensity and imaging a region of the object by scanning the region with an electron beam of a second intensity; wherein the second intensity is lower than the first intensity.

Stage 1530 can include stage 1535 of determining the distance in response to a ratio between at least two out of: (i) amount of particles that passes through the aperture array as a result of the interaction; (ii) amount of particles that did not pass through the aperture array; and (iii) amount of particles generated as result of the interaction.

Stage 1520 can include stage 1526 of measuring a current that flows through at least one detector.

Method 1500 may include at least one of the following stages or a combination thereof: (i) comprising determining the distance in response to a comparison between detection signals generated when the electron beam is positioned in different locations in relation to the aperture; (ii) determining the distance in response to a comparison between detection signals generated when the electron beam illuminates the object at different illumination paths (different angles of incidence, different location in relation to the aperture); (iii) determining the distance in response to a comparison between shadows appearing in different locations of an image of the area of the object; (iv) finding a saturation point; (v) setting a size of the aperture by a shutter and finding a saturation point.

Figure 16:
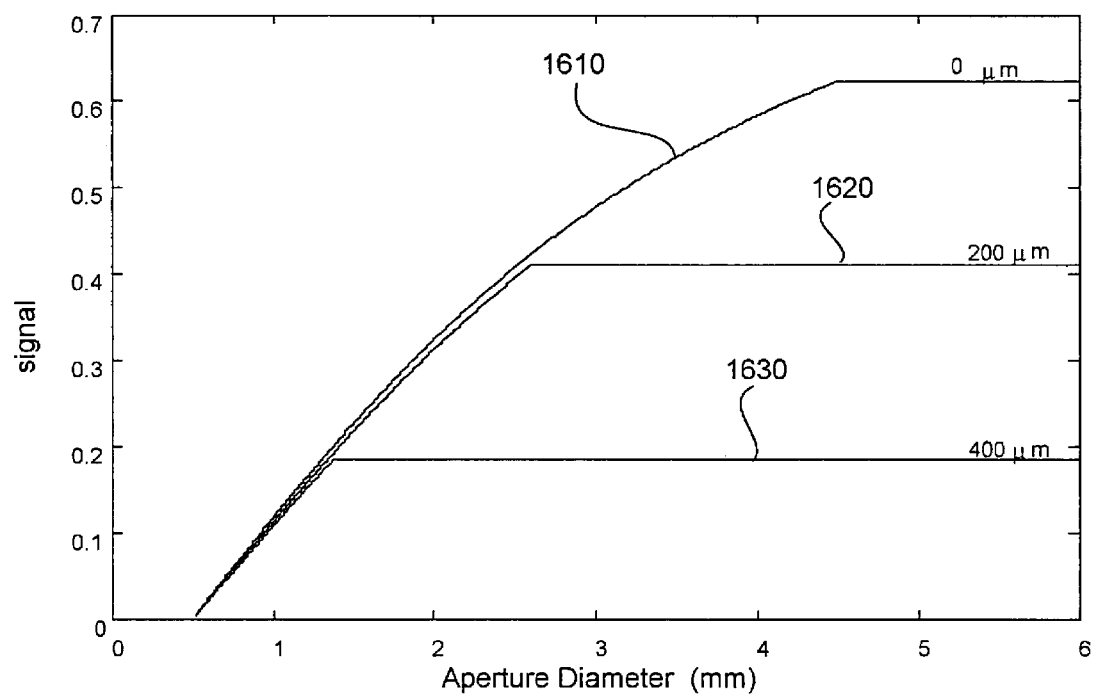
FIG. 16 illustrates an effect of placing a shutter on the collection efficiency according to an embodiment of the invention.

FIG. 16 illustrates an effect of placing a shutter on the collection efficiency according to an embodiment of the invention.

In general, the shutter defines the effective size (and even shape) of an aperture. An aperture of different effective sizes is characterized by different saturation points as illustrated by FIG. 16. According to an embodiment of the invention the working distance can be determined by finding the saturation point. The working distance that corresponds to a saturation point can be set by changing the effective size of the aperture—for example, by closing or opening the shutter.

It is assumed that a detector is placed at a distance of 4 mm above a circular aperture, the shutter is located 2 mm above the aperture and the diameter of the aperture is 250 µm. The collection efficiency dependence on the shutter opening was calculated for three different working distances—0 µm (graph 1610), 20 µm (graph 1620) and 400 µm (graph 1630). It is noted that for different working distances, the saturation point occurs at different shutter diameters.

Figure 17:
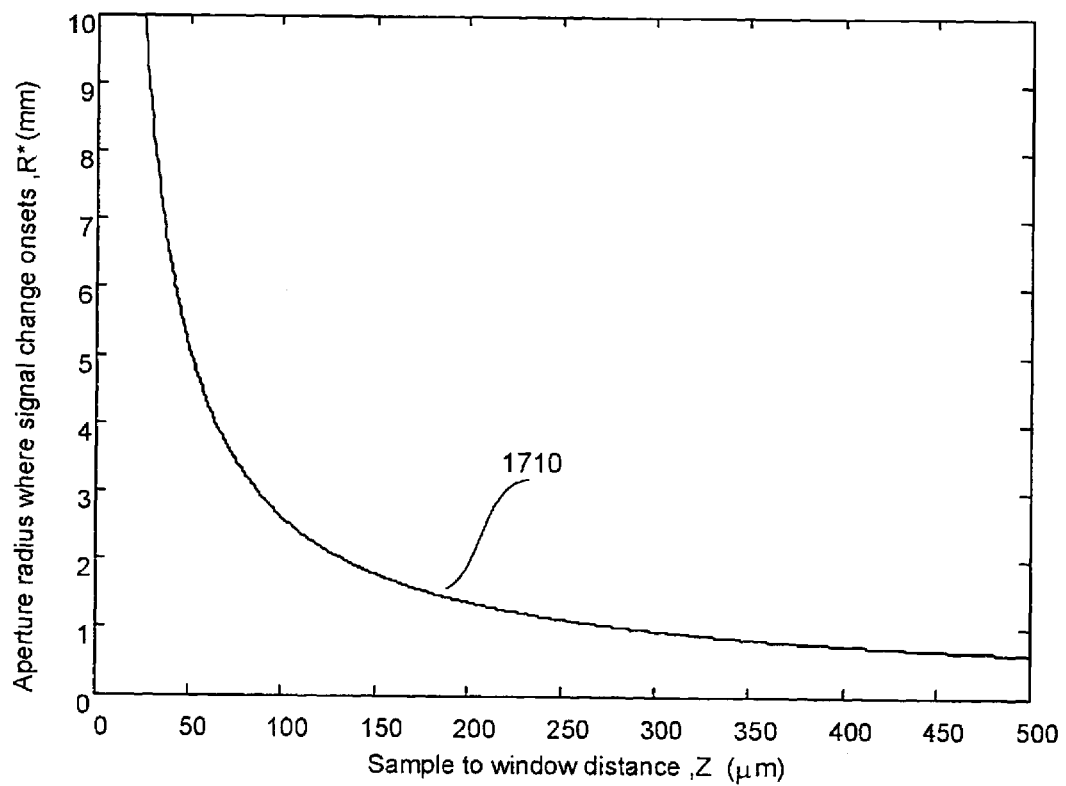
FIG. 17 illustrates a relationship between working distances and a calculated shutter diameter for onset of signal saturation (equilibrium point) according to an embodiment of the invention.

FIG. 17 illustrates a relationship between working distances and a calculated shutter diameter for onset of signal saturation (equilibrium point) according to an embodiment of the invention. The relationship is illustrated by curve 1710.

Figure 18:
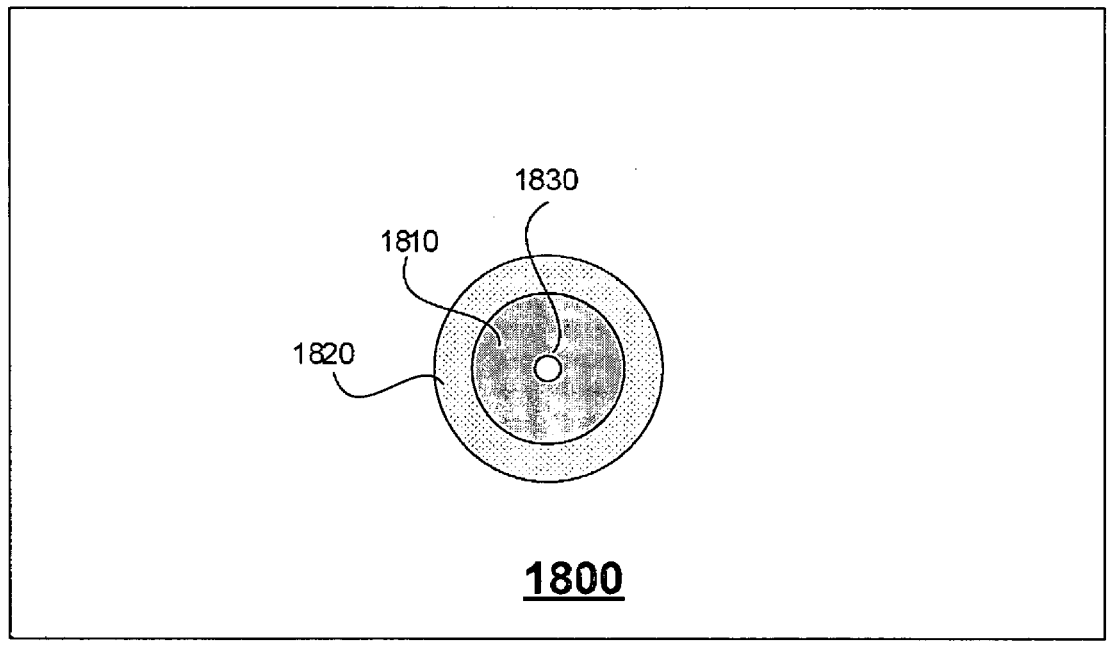
FIG. 18 illustrates a detector that includes two concentric annular detector elements (electrodes) according to an embodiment of the invention.

FIG. 18 illustrates a detector 1800 that includes two concentric annular detector elements (electrodes) 1810 and 1820 according to an embodiment of the invention. The inner annular electrode 1810 surrounds aperture 1830.

Figure 19:
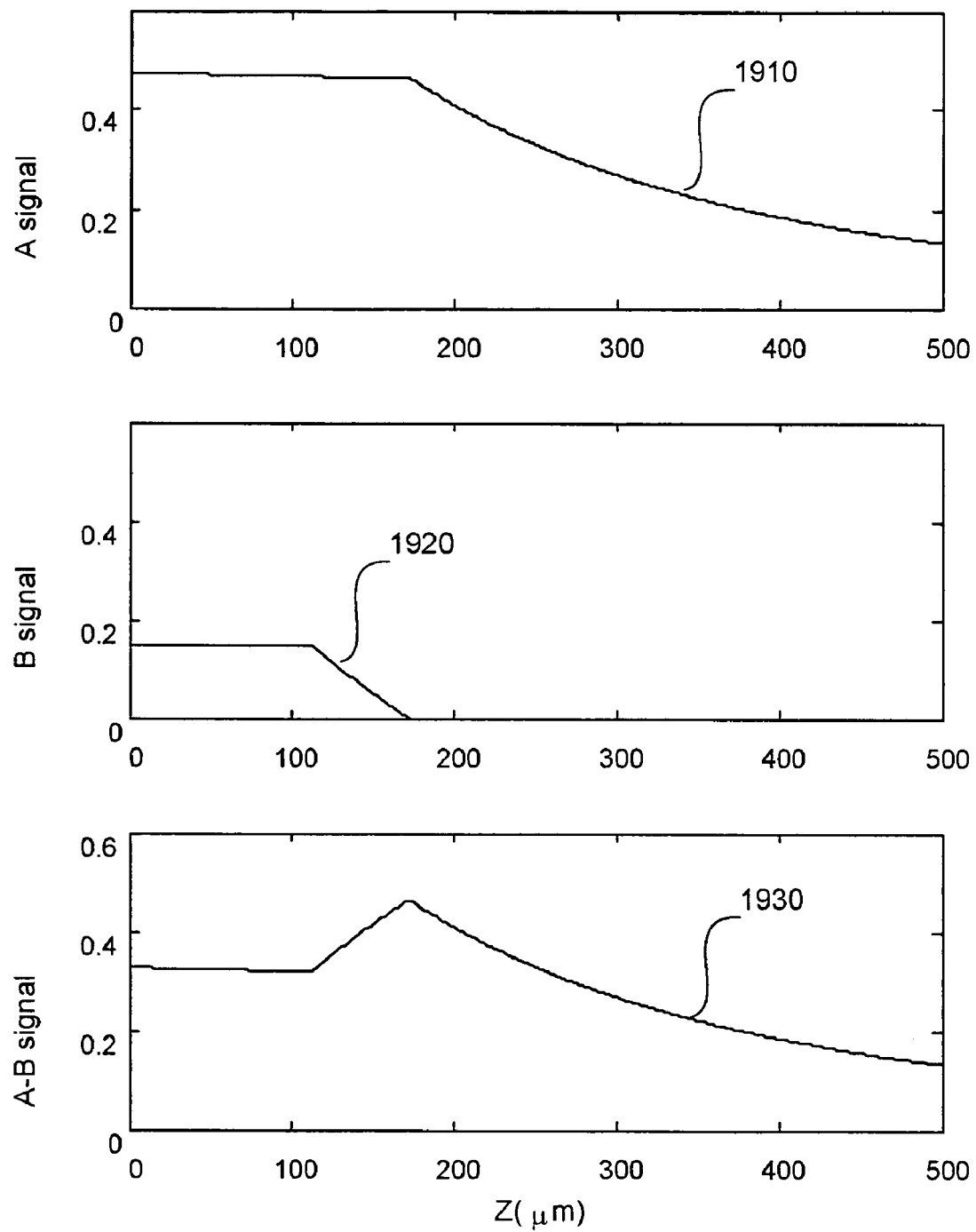
FIG. 19 illustrates collection efficiencies for the detector of FIG. 18, as a function of working distance according to an embodiment of the invention.

FIG. 19 illustrates collection efficiencies for the detector of FIG. 18, as a function of working distance according to an embodiment of the invention.

Detector 1800 is located 4 mm above an aperture of diameter of 250 µm. Inner annular electrode 1810 has a diameter of 6 mm and surrounds aperture 1830 of diameter of 1 mm, and outer annular electrode 1820 has a diameter of 9 mm.

Curve 1910 illustrates detection signals (denoted A) generated by inner annular electrode 1810.

Curve 1920 illustrates detection signals (denoted B) generated by outer annular electrode 1820.

Curve 1930 illustrates the difference (denoted A-B) between detection signals generated by inner annular electrode 1810 and outer annular electrode 1820.

Figure 20:
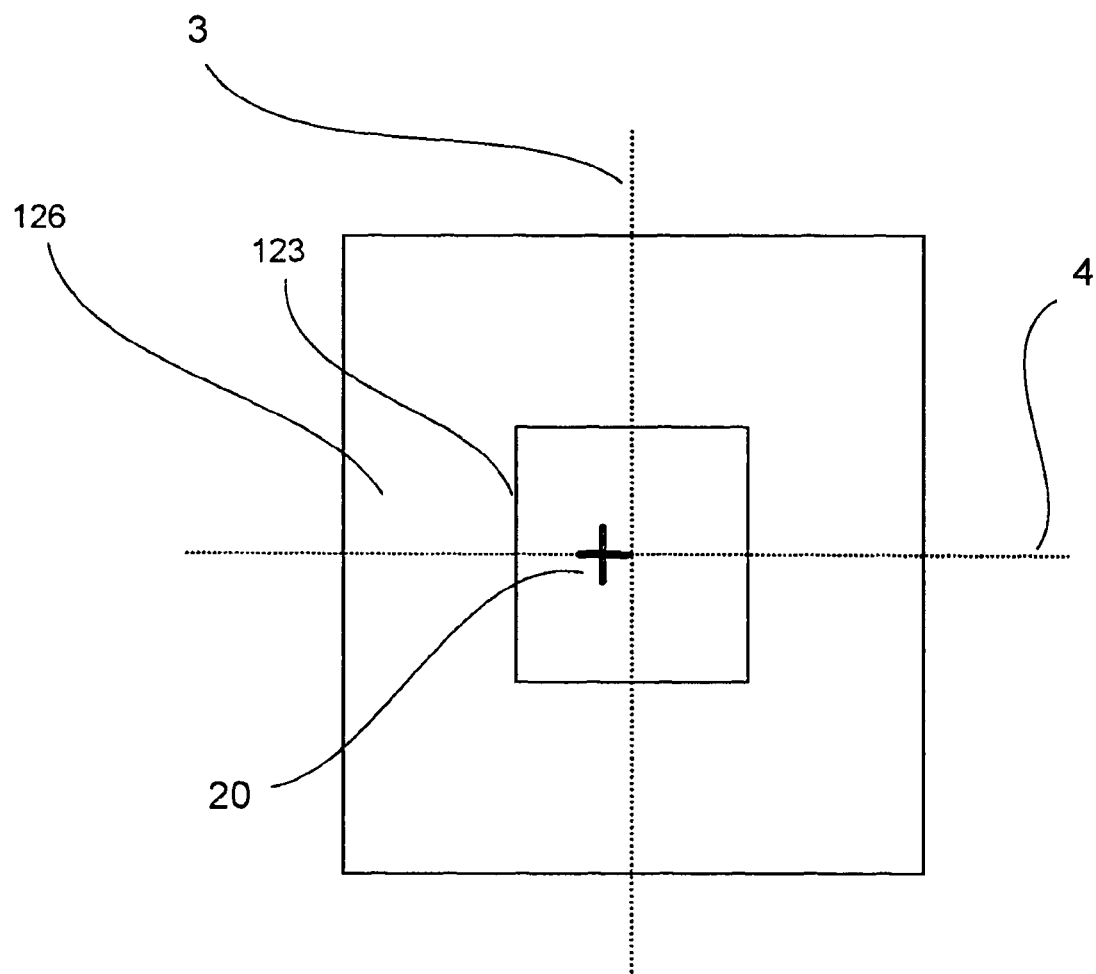
FIG. 20 illustrates an off axis illumination according to an embodiment of the invention.

FIG. 20 illustrates an illumination of electron beam 20 at a location that differs from the center of aperture 123 according to an embodiment of the invention. Aperture 123 is supported by frame 126 and has two axes of symmetry denoted 3 and 4. This illumination is also referred to as off axis illumination.

Figure 21:
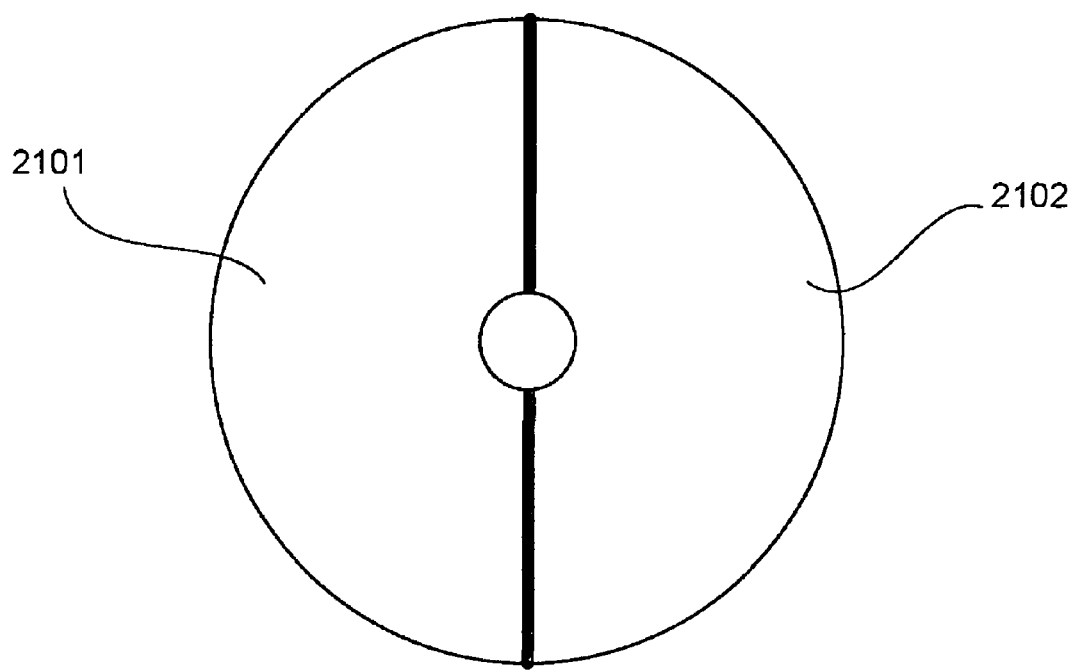
FIG. 21 illustrates an annular BSE detector that has two segments according to an embodiment of the invention.

FIG. 21 illustrates an annular BSE detector 2100 having two segments 2101 and 2102 according to an embodiment of the invention. BSE detector 2100 can be either one of detectors 150 and 160.

Figure 22:
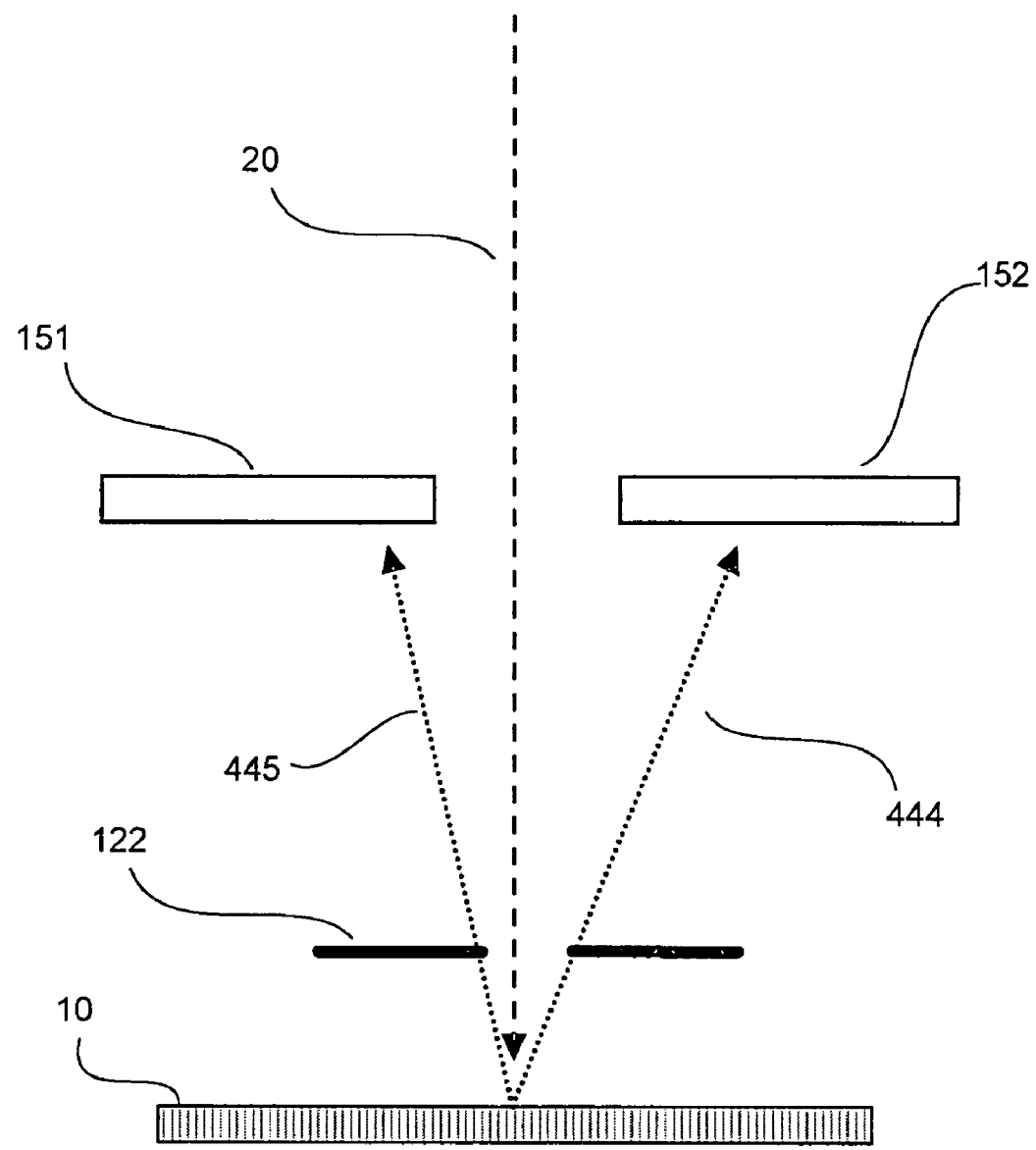
FIG. 22 illustrates an off-axis illumination according to an embodiment of the invention.

FIG. 22 illustrates an off-axis illumination according to an embodiment of the invention.

Electron beam 20 is directed to a location that differs from the middle of aperture 122. Particles such as electrons interact with object 10 and are detected by different portions (different detector elements, different electrodes) 6 and 150. Particles that are directed towards portion 6 are denoted 444 and particles that are directed towards portion 150 are denoted 445.

Figure 23:
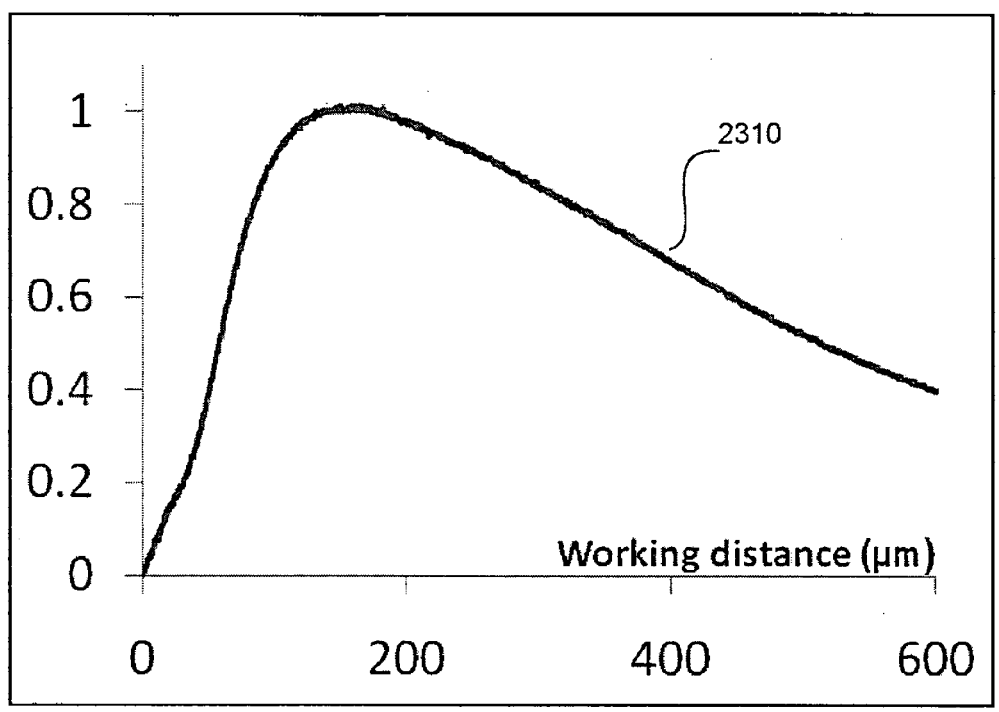
FIG. 23 illustrates a relationship between a difference signal and working distance for off axis illumination according to an embodiment of the invention.

FIG. 23 illustrates a relationship between a difference signal and working distance for off axis illumination according to an embodiment of the invention. Curve 2310 illustrates this relationship. The difference signal grows rapidly till it reaches a maximal value at a working distance of about 150 microns. At distances above 150 microns the difference signal gradually decreases. It is noted that the working distance associated with the maximum may depend only on geometry and is not sensitive to the sample yield or to the intensity of electron beam 20.

The aperture was 250 µm wide and electron beam 20 was positioned 100 microns from the center of the aperture. The difference signal is normalized by its maximal value.

A computer program product can be provided. It includes a computer readable medium that stores instructions for executing any of the mentioned above methods or a combination thereof.

However, other modifications, variations and alternatives are also possible. The specifications and drawings are, accordingly, to be regarded in an illustrative rather than in a restrictive sense.

The present invention can be practiced by employing conventional tools, methodology and components. Accordingly, the details of such tools, component and methodology are not set forth herein in detail. In the previous descriptions, numerous specific details are set forth, in order to provide a thorough understanding of the present invention. However, it should be recognized that the present invention might be practiced without resorting to the details specifically set forth.

Only exemplary embodiments of the present invention and but a few examples of its versatility are shown and described in the present disclosure. It is to be understood that the present invention is capable of use in various other combinations and environments and is capable of changes or modifications within the scope of the inventive concept as expressed herein.

We claim:

1. A method for observing an object that is positioned in a non-vacuum environment, the method comprises:
   generating an electron beam in the vacuum environment
   scanning a region of the object with the electron beam while the object is located below an object holder; wherein the scanning comprises allowing the electron beam to pass through an aperture of an aperture array, pass through an ultra thin membrane that seals the aperture, and pass through the object holder; wherein the ultra thin membrane withstands a pressure difference between the vacuum environment the non-vacuum environment; and
   detecting particles generated in response to an interaction between the electron beam and the object and determining a distance between the object and the ultra-thin membrane in response to detected particles.

2. The method according to claim 1 comprising placing the object such as to contact a lower side of the object holder.

3. The method according to claim 1 comprising placing the object such as to contact a foil of the object holder.

4. The method according to claim 1 comprising scanning the region by a scanning electron microscope and imaging the object by another microscope while the object is located below the object holder.

5. The method according to claim 1 comprising placing the object within a chamber environment and controlling at least one characteristic of the mini environment during the scanning of the region of the object.

6. The method according to claim 5 comprising inducing at least one chemical within the mini environment.

7. The method according to claim 1 comprising scanning regions of multiple objects which are located below the object holder.

8. The method according to claim 1 comprising placing the object within a non-solid entity that contacts a lower side of the object holder and scanning a region of the object.

9. The method according to claim 1 comprising applying force on the object while the object is scanned.

10. A scanning electron microscope comprising:
    an electron beam source positioned in a vacuum environment; the electron beam source is adapted to generate an electron beam;
    an interface between the vacuum environment and a non-vacuum environment in which an object is positioned, the interface comprises an aperture array sealed by an ultra thin membrane that is substantially transparent to the electron beam and withstands a pressure difference between the vacuum environment and the non-vacuum environment;
    an object holder;
    a scanner that scans a region of the object with the electron beam while the object is located below the object holder; wherein the electron beam passes through an aperture of the aperture array, passes through the ultra thin membrane, and passes through the object holder;
    a detector that detects particles generated in response to an interaction between the electron beam and the object and determining a distance between the object and the ultra-thin membrane in response to detected particles.

11. The scanning electron microscope according to claim 10 wherein the object contacts a lower side of the object holder.

12. The scanning electron microscope according to claim 10 wherein the object holder comprises a foil that contacts the object.

13. The scanning electron microscope according to claim 10 comprising a chamber in which the object is maintained during the scanning; wherein the chamber defines a space that is substantially smaller than the non-vacuum environment; wherein the chamber controls a mini environment that surrounds the object.

14. The scanning electron microscope according to claim 10 wherein the chamber comprises a chemical provider that induces at least one chemical within the mini environment.

15. The scanning electron microscope according to claim 10 wherein a lower side of the object holder comprises multiple regions, each region is shaped to contact an object.

16. The scanning electron microscope according to claim 10 wherein the object holder is shaped to contact a non-solid entity in which the object is inserted.

17. The scanning electron microscope according to claim 10 comprising a force applying component for applying force on the object while the object is scanned.

18. The scanning electron microscope according to claim 10 wherein the object holder is rotatable.

19. A method for observing an object that is positioned in a non-vacuum environment, the method comprises:
    illuminating an area of an object with an electron beam; wherein the electron beam is generated in the vacuum environment and passes through an aperture of an aperture array and passes through an ultra thin membrane that seals the aperture; wherein the ultra thin membrane withstands a pressure difference between the vacuum environment and the non-vacuum environment;
    detecting particles generated in response to an interaction between the electron beam and the object; and
    determining a distance between the object and the ultra thin membrane in response to detected particles.

20. The method according to claim 19 comprising illuminating an area of the object by directing the electron-beam to pass through the aperture at a point that differs from a center of the aperture; detecting particles by detectors that have different collection regions; and determining the distance in response to a relationship between detected signals generated by the detectors.

21. The method according to claim 20 comprising determining the distance in response to a difference between detection signals generated by the detectors.

22. The method according to claim 19 comprising detecting particles by at least one detector located in the non-vacuum environment and by at least one detector located in the vacuum environment and determining the distance in response to a relationship between detection signals generated by the detectors.

23. The method according to claim 19 comprising illuminating the area of the object with an electron beam of a first intensity and imaging a region of the object by scanning the region with an electron beam of a second intensity; wherein the second intensity is lower than the first intensity.

24. The method according to claim 19 comprising determining the distance in response to a ratio between at least two out of: (i) amount of particles that passes through the aperture array as a result of the interaction; (ii) amount of particles that did not pass through the aperture array; and (iii) amount of particles generated as result of the interaction.

25. The method according to claim 19 comprising measuring a current that flows through at least one detector.

26. The method according to claim 19 comprising performing multiple iterations of illuminating and detecting; wherein at least one iteration is preceded by altering a distance between an object and the ultra thin membrane; and determining a distance between the object and the ultra thin membrane in response particles detected during a plurality of iterations.

27. The method according to claim 19 comprising altering the distance until a relationship between particles that pass through the aperture array and particles that not pass through the aperture array maintains constant despite the altering of the distance.

28. A scanning electron microscope comprising:
an electron beam source positioned in a vacuum environment; the electron beam source is adapted to generate an electron beam;
optics configured to direct the electron beam towards an area of the object;
an interface between the vacuum environment and a non-vacuum environment in which an object is positioned, the interface comprises an aperture array sealed by an ultra thin membrane that is substantially transparent to the electron beam and withstands a pressure difference between the vacuum environment and the non-vacuum environment;
at least one detector that detects particles generated in response to an interaction between the electron beam and the object; and
a controller configured to determine a distance between the object and the ultra thin membrane in response to detection signals generated by the at least one detector.

29. The scanning electron microscope according to claim 28 wherein the optics direct the electron beam to the area by passing through the aperture at a point that differs from a center of the aperture; wherein the at least one detector comprises detectors that have different collection regions; and the controller determines the distance in response to a relationship between detection signals generated by the detectors.

30. The scanning electron microscope according to claim 29 wherein the controller determines the distance in response to a difference between detection signals generated by the detectors.

31. The scanning electron microscope according to claim 28 comprising at least one detector located in the non-vacuum environment and at least one detector located in the vacuum environment.

32. The scanning electron microscope according to claim 28 wherein the scanning electron microscope illuminates the area of the object with an electron beam of a first intensity; wherein the optics image a region of the object by scanning the region with an electron beam of a second intensity; wherein the second intensity is lower than the first intensity.

33. The scanning electron microscope according to claim 28 wherein the controller determines the distance in response to a ratio between at least two out of: (i) amount of particles that passes through the aperture array as a result of the interaction; (ii) amount of particles that did not pass through the aperture array; and (iii) amount of particles generated as result of the interaction.

34. The scanning electron microscope according to claim 28 comprising a detector that has current measurement capabilities.

35. The scanning electron microscope according to claim 28 comprising a distance altering unit configured to alter the distance between the object and the ultra thin membrane; wherein the scanning electron microscope performs multiple iterations of illuminating the area of the object and detecting particles; wherein at least one iteration is preceded by altering a distance between an object and the ultra thin membrane; wherein the controller determines the distance between the object and the ultra thin membrane in response particles detected during a plurality of iterations.

36. The scanning electron microscope according to claim 28 wherein the distance altering unit alters the distance until a relationship between particles that pass through the aperture array and particles that not pass through the aperture array maintains constant despite the altering of the distance.

37. A method for aligning an electron beam and an aperture of an aperture array, the method comprises:
obtaining an image of a first area of the aperture array; wherein the first area comprises multiple apertures of the aperture array;
calculating a spatial relationship between a selected aperture of the multiple apertures and a reference location within the first area;
aligning an electron beam with the reference location in response to the spatial relationship; and
obtaining an image of a region of an object that is positioned in a non-vacuum environment; wherein the obtaining comprises scanning the region by an electron beam that is generated in a vacuum environment, passes through the selected aperture and passes through an ultra thin membrane that seals the selected aperture; wherein the ultra thin membrane withstands a pressure difference between the vacuum environment and the non-vacuum environment.

38. The method according to claim 37 comprising obtaining the image by scanning a second area of the aperture array; wherein the second area is smaller than the first area.

39. The method according to claim 37 wherein the aligning comprises moving the aperture array.

40. A scanning electron microscope comprising:
an electron beam source positioned in a vacuum environment; the electron beam source is adapted to generate an electron beam;
an interface between the vacuum environment and a non-vacuum environment in which an object is positioned, the interface comprises an aperture array sealed by an ultra thin membrane that is substantially transparent to the electron beam and withstands a pressure difference between the vacuum environment and the non-vacuum environment;
optics configured to scan, with an electron beam, a first area of the aperture array and scan a second area of the aperture array; wherein the first area comprises multiple apertures of the aperture array; wherein the second area is smaller than the first area and comprises a selected aperture;
at least one detector that detects particles generated in response to an interaction between the electron beam and at least one entity out of the interface and the object; and
a controller configured to:
calculate a spatial relationship between a selected aperture of the multiple apertures and a reference location within the first area; and
control an alignment of the electron beam with the reference location in response to the spatial relationship.

41. The scanning electron microscope according to claim 40 comprising an alignment unit that moves the aperture array during the alignment.

42. The method according to claim 1 wherein the object comprises a solution of an electrochemical cell.

43. The method according to claim 1 wherein the object comprises a solution of an electrochemical cell and an electrode of the electrochemical cell supports the object holder.

44. The method according to claim 1 wherein the object comprises a solution of an electrochemical cell; wherein the solution is placed below the object holder and an electrode of the electrochemical cell contacts the solution.

45. The scanning electron microscope according to claim 10 wherein the object comprises a solution of an electrochemical cell.

46. The scanning electron microscope according to claim 10 wherein the object comprises a solution of an electrochemical cell and an electrode of the electrochemical cell supports the object holder.

47. The scanning electron microscope according to claim 10 wherein the object comprises a solution of an electrochemical cell; wherein the solution is placed below the object holder and an electrode of the electrochemical cell contacts the solution.

48. The method according to claim 19 comprising determining the distance in response to a ratio between detection signals generated by the detectors.

49. The method according to claim 19 comprising illuminating an area of the object; detecting particles by detectors that have different solid angles; and determining the distance in response to a relationship between detected signals generated by the detectors.

50. The scanning electron microscope according to claim 28 wherein the controller is adapted to determine the distance in response to a ratio between detection signals generated by the detectors.

51. The scanning electron microscope according to claim 28 wherein the optics are configured to illuminate an area of the object; wherein the scanning electron microscope comprises detectors that have different solid angles; and wherein the controller is adapted to determine the distance in response to a relationship between detected signals generated by the detectors.

52. The method according to claim 19 comprising determining the distance in response to a comparison between detection signals generated when the electron beam is positioned in different locations in relation to the aperture.

53. The method according to claim 19 comprising determining the distance in response to a comparison between detection signals generated when the electron beam illuminates the object at different illumination paths.

54. The method according to claim 19 comprising determining the distance in response to a comparison between shadows appearing in different locations of an image of the area of the object.

55. The scanning electron microscope according to claim 28 wherein the controller is adapted to determine the distance in response to a comparison between detection signals generated when the electron beam is positioned in different locations in relation to the aperture.

56. The scanning electron microscope according to claim 28 wherein the controller is adapted to determine the distance in response to a comparison between detection signals generated when the electron beam illuminates the object at different illumination paths.

57. The scanning electron microscope according to claim 28 wherein the controller is adapted to determine the distance in response to a comparison between shadows that appear in different locations of an image of the area of the object.

58. The method according to claim 19 comprising finding a saturation point.

59. The method according to claim 19 comprising setting a size of the aperture by a shutter and finding a saturation point.

60. The scanning electron microscope according to claim 28 wherein the controller is adapted to determine the distance by finding a saturation point.

61. The scanning electron microscope according to claim 28 wherein the controller is adapted to determine the distance in response to a size of the aperture and in response to a saturation point; wherein the size of the aperture is set by a shutter.

* * * * *